US011254734B2

(12) United States Patent
Neugebauer et al.

(10) Patent No.: US 11,254,734 B2
(45) Date of Patent: Feb. 22, 2022

(54) FAB MOLECULES WITH A RODENT HINGE REGION AND A NON-RODENT CH1 REGION

(71) Applicant: MorphoSys AG, Planegg (DE)

(72) Inventors: Julia Neugebauer, Munich (DE); Steffen Runz, Munich (DE); Stefanie Urlinger, Munich (DE)

(73) Assignee: MORPHOSYS AG, Planegg (DE)

( * ) Notice: Subject to any disclaimer, the term of this patent is extended or adjusted under 35 U.S.C. 154(b) by 79 days.

(21) Appl. No.: 16/348,941

(22) PCT Filed: Nov. 13, 2017

(86) PCT No.: PCT/EP2017/078991
§ 371 (c)(1),
(2) Date: May 10, 2019

(87) PCT Pub. No.: WO2018/087349
PCT Pub. Date: May 17, 2018

(65) Prior Publication Data

US 2019/0345236 A1 Nov. 14, 2019

(30) Foreign Application Priority Data

Nov. 14, 2016 (EP) .................................... 16198591

(51) Int. Cl.
*C07K 16/18* (2006.01)

(52) U.S. Cl.
CPC .......... *C07K 16/18* (2013.01); *C07K 2317/24* (2013.01); *C07K 2317/522* (2013.01); *C07K 2317/53* (2013.01); *C07K 2317/55* (2013.01)

(58) Field of Classification Search
CPC ............ C07K 2317/55; C07K 2317/53; C07K 2317/522; C07K 2317/24
USPC ....................................................... 424/138.1
See application file for complete search history.

(56) References Cited

U.S. PATENT DOCUMENTS 10,662,254 B2* 5/2020 Meng ...................... A61P 43/00
2020/0308304 A1* 10/2020 Meng ................. C07K 16/4283

FOREIGN PATENT DOCUMENTS

WO 2016/081746 5/1916
WO 94/11028 5/1994
WO 01/05950 1/2001
WO 2011/073954 6/2011

OTHER PUBLICATIONS

International Search Report and Written Opinion in PCT/EP2107/078991 dated Jan. 23, 2018.
International Preliminary Report on Patentability in PCT/EP2107/078991 dated May 14, 2019.
Christopoulos, C. "Platelet surface IgG in patients receiving infusions of Fab fragments of a chimaeric monoclonal antibody to glycoprotein IIb-IIIa" Clin. Exp. Immunol. 1994 98:6-11.
Edelman et al. "The Covalent Structure of an Entire γG Immunoglobulin Molecule" Biochemistry 1969 63:78-85.
Jefferis, R. & LeFranc, M. "Human immunoglobulin allotypes" mAbs 2009 1(4):1-7.
Kim et al. "Evading pre-existing anti-hinge antibody binding by hinge engineering" mAbs 2016 8(8):1536-1547.
Kormeier et al. "Specificty of Antiglobulin Factors in Normal Human Serum Reacting with Enzyme Digested γG-globulin" The Journal of Immunology 1968 100(3):612-621.
Larrick, J.W. & Fry, K.E. "Recombinant antibodies" Hum. Antibod. Hybridomas 1991 2:172-189.
Persselin, J.E. & Stevens, R.H. "Anti-Fab Antibodies in Humans Predominance of Mino Immunoglobulin G Subclasses in Rheumatoid Arthritis" J. Clin. Invest. 1985 76:723-730.
Rothlisberger et al. "Domain Interactions in the Fab Fragment: A Comparative Evaluation of the Single-chain Fv and Fab Format Engineered with Variable Domains of Different Stability" J. Mol. Biol. 2005 347:773-789.
Tiller et al. "A fully synthetic human Fab antibody library based on fixed VH/VL framework pairings with favorable biophysical properties" mAbs 2013 5(3):445-470.
Van Schie et al. "Cross-reactive and pre-existing antibodies to therapeutic antibodies—Effects on treatment and immunogenicity" mAbs 2015 7(4):662-671.
Winter, G. & Milstein, C. "Man-made antibodies" Nature 1991 349(24):293-299.

* cited by examiner

*Primary Examiner* — Lynn A Bristol
(74) *Attorney, Agent, or Firm* — Licata & Tyrrell P.C.

(57) ABSTRACT

The disclosure relates to novel Fab molecules comprising a modified heavy chain constant region. The modified constant region prevents the recognition of the Fab molecules by anti-Fab antibodies present in a host's serum. The disclosure further relates to methods of generating such modified Fab molecules for biological, diagnostic, pharmaceutical and other uses.

7 Claims, 9 Drawing Sheets

Figure 2A:
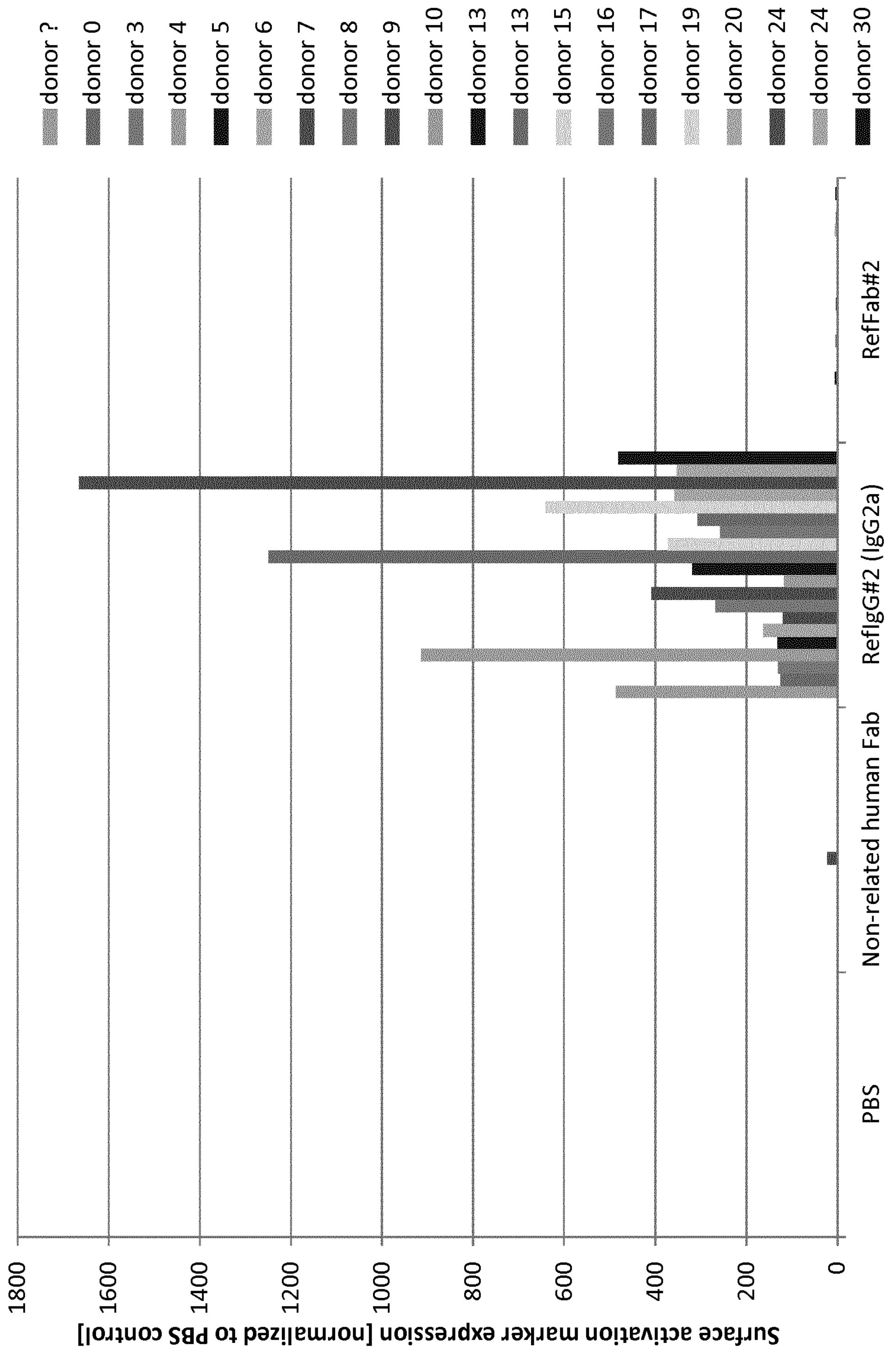

Specification includes a Sequence Listing.

Figure 1

| | | C-terminal region of human CH1 | | | | | | | Hinge region | | | | | | | | | | |
|---|---|---|---|---|---|---|---|---|---|---|---|---|---|---|---|---|---|---|---|
| SEQ ID NO. | Construct / EU Numbering | ... | 210 | 211 | 212 | 213 | 214 | 215 | 216 | 217 | 218 | 219 | 220 | 221 | 222 | 223 | 224 | 225 | 226 |
| | | | | | | | | | truncated hu IgG1 hinge | | | | | | | | | | |
| 95 | huFab [CH1 / Hinge(IgG1)] | ... | K | V | D | K | K | V | E | P | K | S | C | | | | | | |
| 96 | huFab [CH1(K214R) / Hinge(IgG1)] | ... | K | V | D | K | R | V | E | P | K | S | C | | | | | | |
| | | | | | | | | | truncated rat IgG2a hinge sequences | | | | | | | | | | |
| 97 | Fab [CH1(V215I) / Hinge(rat IgG2a)] | ... | K | V | D | K | K | I | V | P | R | E | C | | | | | | |
| | | | | | | | | | truncated rat IgG2b hinge sequences | | | | | | | | | | |
| 98 | Fab [CH1 / Hinge(rat IgG2b)] | ... | K | V | D | K | K | V | E | R | R | N | G | G | I | G | H | K | C |
| 99 | Fab [CH1(D212E) / Hinge(rat IgG2b)] | ... | K | V | E | K | K | V | E | R | R | N | G | G | I | G | H | K | C |
| 100 | Fab [CH1(K214G) / Hinge(rat IgG2b)] | ... | K | V | D | K | G | V | E | R | R | N | G | G | I | G | H | K | C |
| 101 | Fab [CH1(K214E) / Hinge(rat IgG2b)] | ... | K | V | D | K | E | V | E | R | R | N | G | G | I | G | H | K | C |
| 102 | Fab [CH1/ Hinge(R217E)(rat IgG2b)] | ... | K | V | D | K | K | V | E | E | R | N | G | G | I | G | H | K | C |
| 103 | [CH1(K214E)/ Hinge(N219Q)(rat IgG2b)] | ... | K | V | D | K | E | V | E | R | R | Q | G | G | I | G | H | K | C |

Figure 6
A
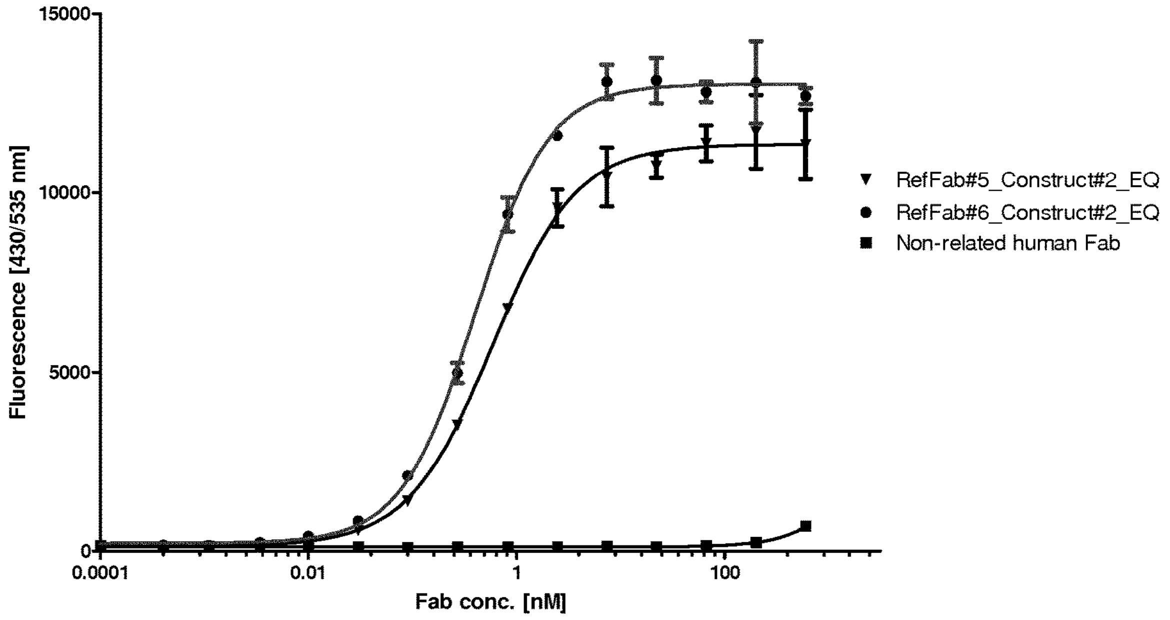
B
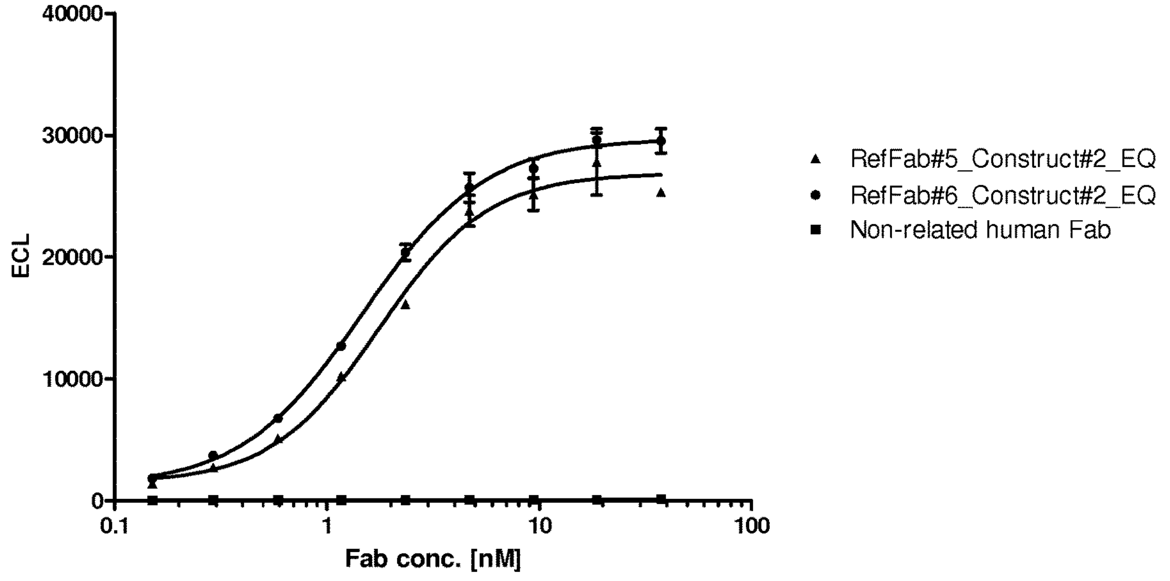

FAB MOLECULES WITH A RODENT HINGE REGION AND A NON-RODENT CH1 REGION

This patent application is the National Stage of International Application No. PCT/EP2017/078991 filed Nov. 13, 2017, which claims the benefit of EP 16198591.6 filed Nov. 14, 2016, teachings of each of which are incorporated herein by reference in their entirety.

FIELD OF THE INVENTION

The present application relates to Fab molecules comprising a modified heavy chain constant region. The modified heavy chain constant region prevents the recognition of the Fab molecules by pre-existing or newly formed anti-Fab antibodies present in a host's serum. In particular, it prevents receptor activation through anti-Fab antibody induced receptor clustering. The present disclosure further relates to methods of generating such Fab molecules for biological, diagnostic, pharmaceutical and other uses.

BACKGROUND OF THE INVENTION

Fabs can be obtained from any immunoglobulin, especially from a monoclonal antibody, using any suitable standard enzymatic cleavage and/or digestion techniques, for example by treatment with papain. Treatment with papain can be used to cleave an immunoglobulin into two Fab fragments and an Fc fragment. The enzymatic cleavage typically results in a Fab comprising an intact CL and CH1 domain, wherein the CH1 domain is usually extended by additional amino acids of the IgG hinge region. Alternatively, a Fab can be prepared by the use of recombinant DNA techniques involving the manipulation and re-expression of DNA encoding the Fab variable and constant regions providing flexibility in defining the length of the included hinge region.

Fabs which in nature do exist only as a degradation product of immunoglobulins lack the Fc-part and expose a novel C-terminal end which forms an epitope that may be recognized by antibodies present in a host's serum which may elicit an immune response. It has been observed that the amino acid sequence near the papain cleavage site which lies within the hinge region of a human IgG, is reactive with pre-existing anti-Fab antibodies present in human serum. Amino acid sequences that form the epitopes for such anti-IgG fragment or anti-Fab antibodies can be referred to as auto-antigenic sequences (Kormeier et al. (1968) J. Immunol. 100(3); 612-21; Persselin and Stevens (1985) J. Clin. Invest. 76; 723-30). Aside the presence of pre-existing antibodies, Christopoulos and coworkers (Christopoulos C, et al., Clin. Exp. Immunol. 1994 October; 98 (1):6-11.1994) also demonstrated that the C-terminal end of a Fab may also act as a preferred epitope for the generation of newly formed antibodies which react with the auto-antigenic Fab sequence. In accordance with these findings, the inventors of the present disclosure determined that also recombinant generated human Fab molecules, whose heavy chain constant region C-terminally ends within the hinge region of an IgG are recognized by anti-Fab antibodies present in human serum.

With the development of Fabs as therapeutics, the existence of anti-Fab antibodies complicates the usage of such therapeutic molecules. Recognition by anti-Fab antibodies can change the pharmacokinetics and/or pharmacodynamics of such molecules (e.g. receptor activation instead of inhibition), formation new complexes and functions (e.g. adding an antibody Fc-part with all its effector functions) and changes in the size of the complex which may also have consequences for tissue distribution. Therefore, this phenomenon represents a significant safety and efficacy risk which needs to be avoided.

In order to minimize such a risk, the formation of an epitope that is recognized by anti-Fab antibodies can be avoided by replacing one or more amino acid at the C-terminal end of a Fab heavy chain with an amino acid sequence which is not recognized by pre-existing anti-Fab antibodies. More specifically, the exchange of the hinge region (e.g., a human hinge region) with one more amino acids of a hinge region from a distinct species (e.g., from a rodent species) may prevent binding or recognition of anti-Fab antibodies present in a host's serum (e.g., human serum) and thus may be suited to avoid the above mentions risks for using Fabs as therapeutics.

Modified Fab heavy chain constant regions rendering an immunogenic compound less immunogenic in a particular host has been disclosed. In WO94/11028, an auto-antigenic sequence derived from the human IgG1 constant region was fused to the C-terminal end of a murine Fab fragment. The thus obtained modified murine Fab fragment appeared less immunogenic in human when compared to its corresponding non-modified mouse Fab molecule.

WO2011073954 describes Fab molecules wherein a polyhistidine tag or a glycine-serine tag was attached to the C-terminal end of the Fab heavy chain. The attached tags prevented binding of pre-existing anti-Fab antibodies to the modified Fab. However, of the significantly increased size of the Fab molecule, the addition of an artificial sequence bears a high risk in provoking an immune response against said newly introduced amino acid sequence.

Kim and co-workers (MAbs. 2016 Aug. 9:1-12) suggest the generic use of human Fab molecules of the IgG2 or IgG4 isotype or to introduce particular mutations and/or truncations in the hinge region of a human Fab of the IgG1 isotype, in order to prevent the binding of anti-Fab antibodies present in human serum.

Accordingly, a need exists for further improved Fab molecules lacking of Fab specific epitopes that can be recognized by pre-existing or newly generated anti-Fab antibodies present in a host's serum and which efficiently prevent target receptor activation due to the presence of anti-Fab antibodies.

FIGURE LEGENDS

FIG. 1: Amino acid sequences of the C-terminal region of modified heavy chain constant regions according to the present disclosure.

SEQ ID NO: 95 refers to the C-terminal heavy chain constant region of a human Fab comprising a human IgG1 CH1 domain and hinge region according SEQ ID NO: 1. The hinge region C-terminally ends with a cysteine at EU position 220.

SEQ ID NO: 96 is similar to SEQ ID NO: 95 with the difference of a natural occurring K214R mutation in the CH1 domain (allotype).

SEQ ID NO: 97 refers to the C-terminal heavy chain constant region of a modified human constant region according SEQ ID NO: 70. EU position 216-220 of the human Fab hinge region of the IgG1 isotype are exchanged with 5 amino-acid residues of a corresponding rat IgG2a hinge region. In addition, the human CH1 domain bears a V215I mutation in accordance with the presence of an isoleucine at position 215 in the natural occurring rat IgG2a CH1 domain.

SEQ ID NO: 98 refers to the C-terminal heavy chain constant region of a modified human constant region according SEQ ID NO: 71. EU position 216-220 of a human Fab hinge region of the IgG1 isotype are exchanged with 11 amino-acid residues of a corresponding rat IgG2b hinge region.

SEQ ID NO: 99 is similar to SEQ ID NO: 98 but with an additional D212E mutation in the human CH1 domain in order to resolve a potential T-cell epitope present in SEQ ID NO: 71.

SEQ ID NO: 100 is similar to SEQ ID NO: 98 but with an additional K214G mutation in the human CH1 domain to resolve a potential T-cell epitope present in SEQ ID NO: 71.

SEQ ID NO: 101 is similar to SEQ ID NO: 98 but with an additional K214E mutation in the human CH1 domain to resolve a potential T-cell epitope present in SEQ ID NO: 71.

SEQ ID NO: 102 is similar to SEQ ID NO: 98 but with an additional R217E mutation in the rat IgG2b hinge region to resolve a potential T-cell epitope present in SEQ ID NO: 71.

SEQ ID NO: 103 is similar to SEQ ID NO: 101 but with an additional N219Q mutation in the hinge region to remove a potential posttranslational modification site present in SEQ ID NO: 74.

Figure 2B:
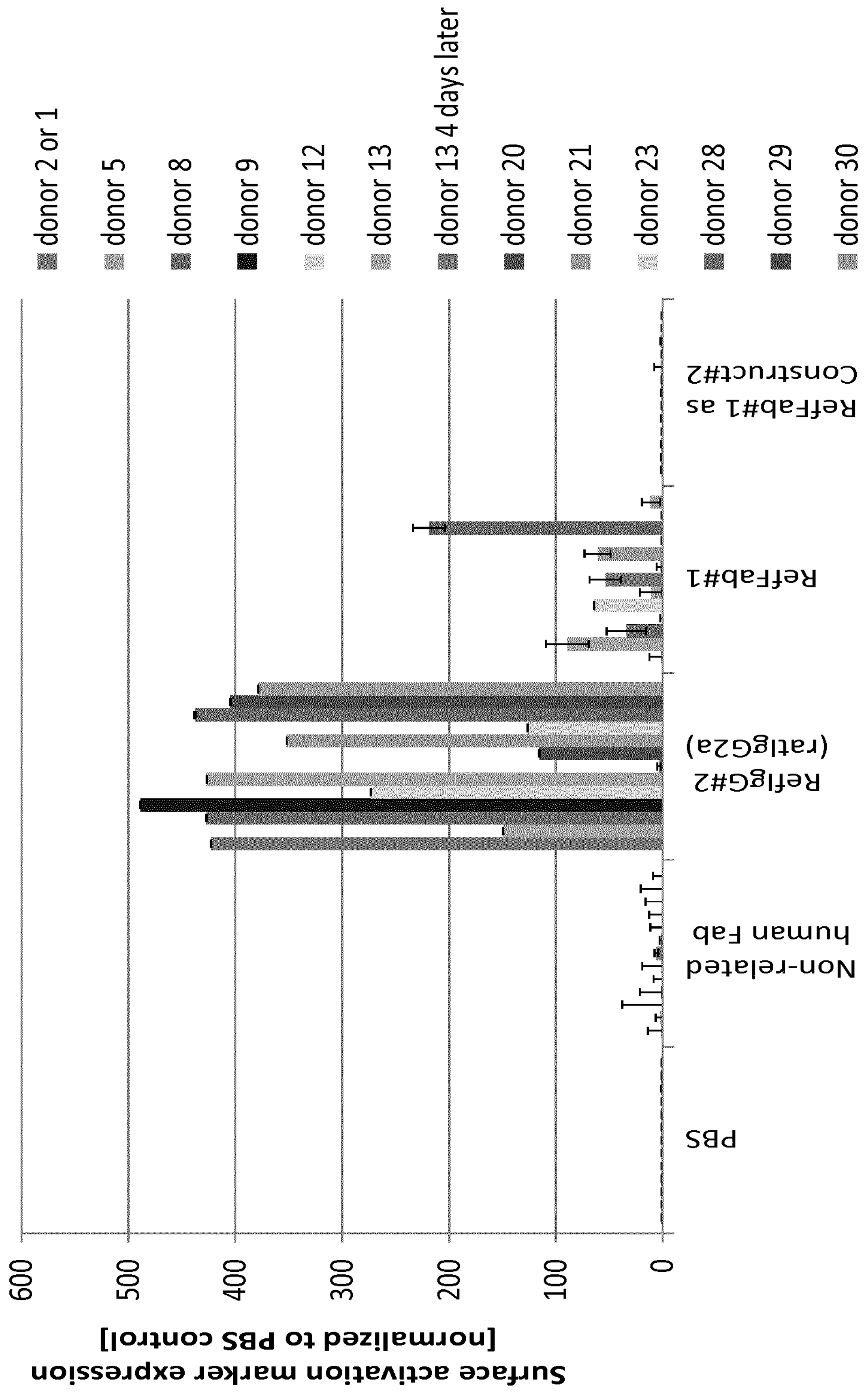
Figure 2C:
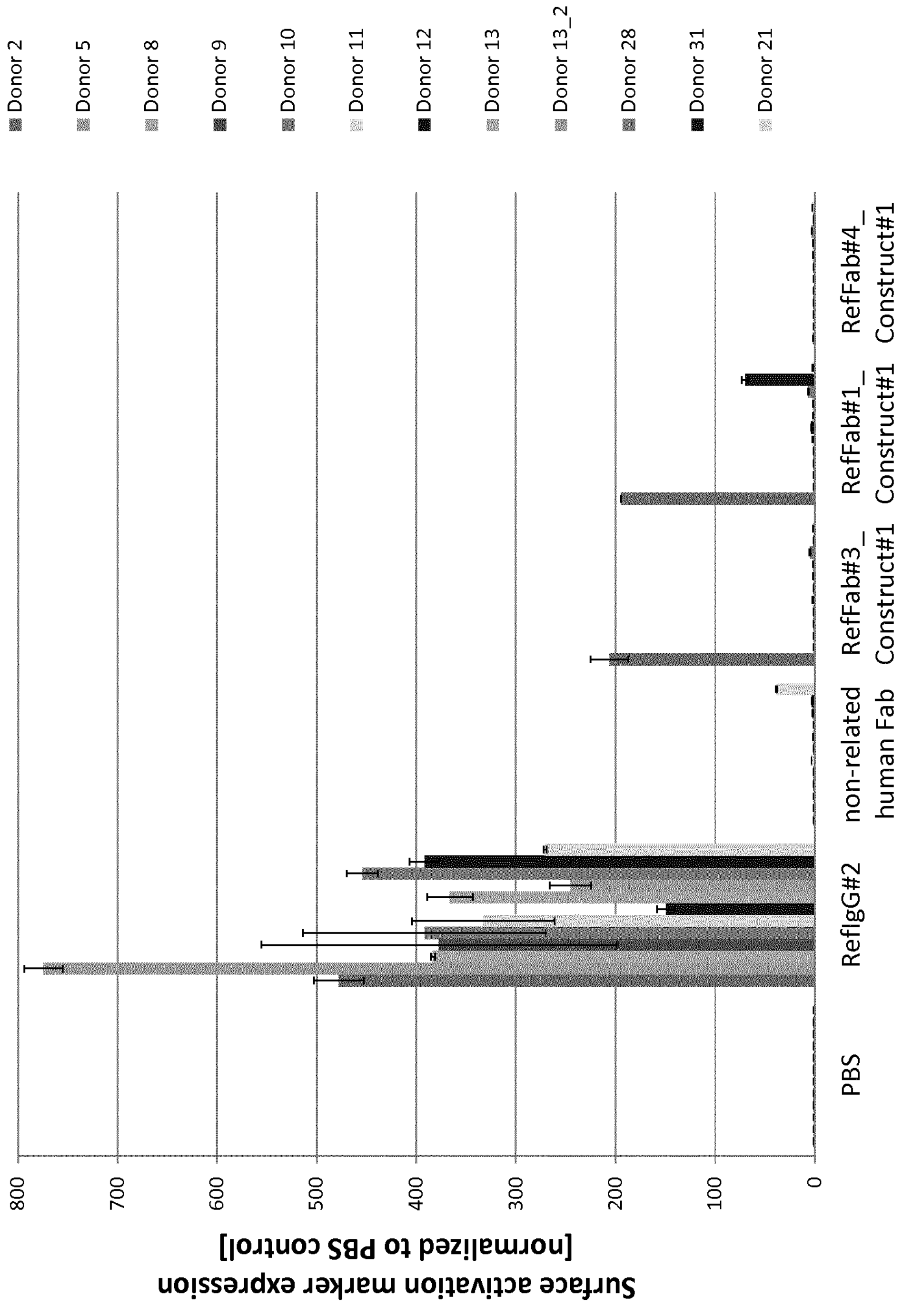

FIG. 2: FACS based functional characterization of Fab molecules of the present disclosure for their ability to induce receptor activation through pre-existing anti-Fab antibodies present in human plasma samples.

A) A rat derived Receptor-X specific IgG (Ref-IgG#2) induces strong expression of a cell surface activation marker whereas the corresponding rat derived Fab molecule (Ref-Fab#2) shows no effect on receptor activation in the presence of human plasma samples.

B) A Receptor-X specific human Fab (Ref-Fab#1) comprising a human CH1 and human hinge region induces significant expression of the cell surface activation marker in presence of 8 of 13 tested human plasma samples. In contrast, a Fab with identical variable domains but with a rat IgG2b hinge region (SEQ ID NO: 71; Construct#2) reveals no receptor activation.

C) 3 distinct Receptor-X specific Fabs (Ref-Fab#1, Ref-Fab#3, Ref-Fab#4) comprising a human CH1 domain and a rat IgG2a hinge region (SEQ ID NO: 70; Construct#1) induce expression of a cell surface activation marker only in the presence of 1-2 of 12 tested human plasma samples.

Figure 3:
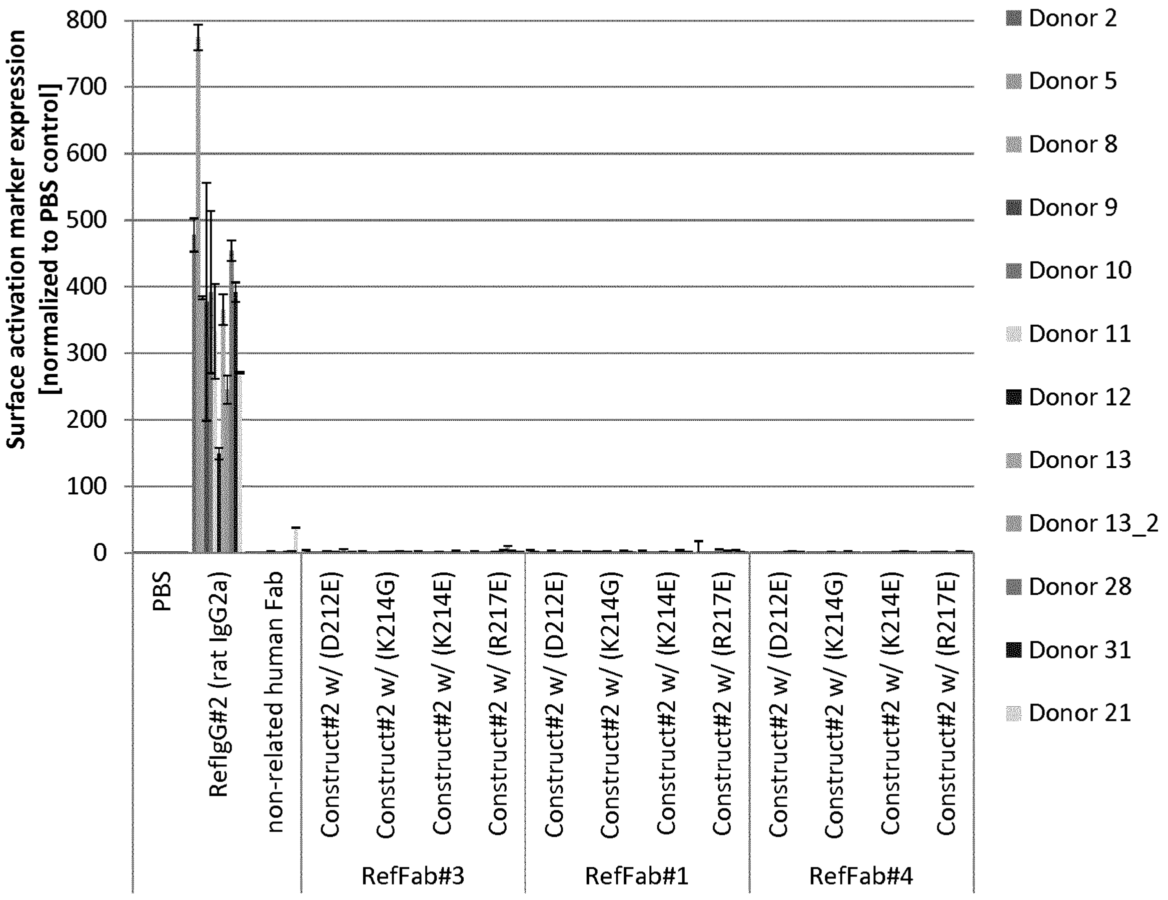

FIG. 3: FACS based functional characterization of various Fab and IgG molecules of the present disclosure for their ability to induce receptor activation through pre-existing anti-Fab antibodies present in different human plasma samples. None of the 3 distinct Receptor-X specific Fabs (Ref-Fab#1, Ref-Fab#3, and Ref-Fab #4) comprising a modified heavy chain constant region comprising according SEQ ID NO: 72-75 (Construct#2) induce expression of the cell surface activation marker in presence of 12 tested human serum samples. The introduced mutations in the human CH1 domain or in the rat IgG2b hinge region resolves a potential T-cell epitope present in SEQ ID NO: 71.

Figure 4:
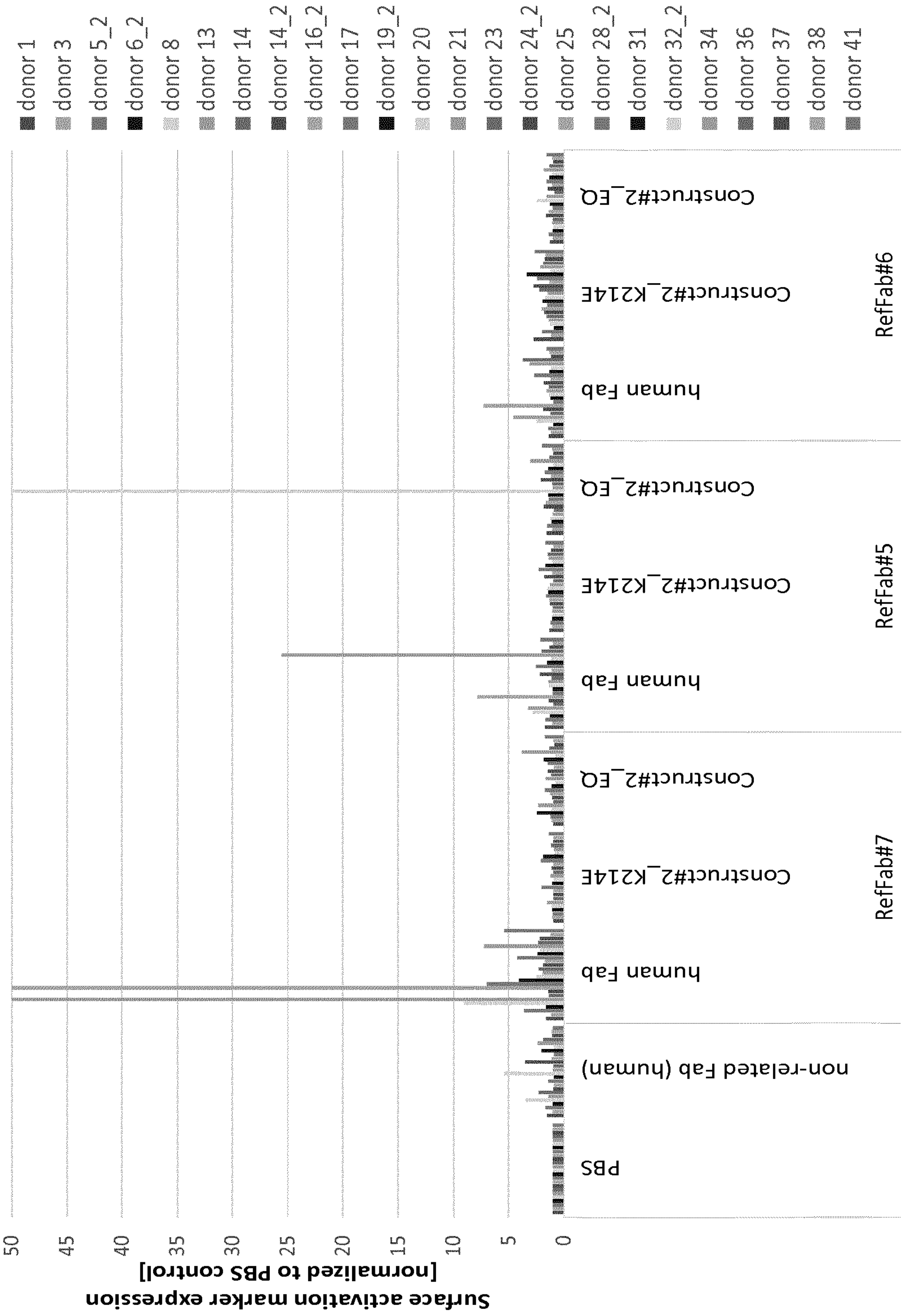

FIG. 4: FACS based functional characterization of various Fab molecules of the present disclosure for their ability to induce receptor activation through pre-existing anti-Fab antibodies present in human serum samples. 3 distinct Receptor-X specific Fabs (Ref-Fab#5, Ref-Fab#6, Ref-Fab#7) comprising a modified human constant region according SEQ ID NO: 74 and SEQ ID NO: 76 (removal of additional posttranslational modification site present in SEQ ID NO: 74) were compared to their fully human Fab counterpart. For all 3 Fabs, the fully human constructs induced strong receptor activation in the presence of at least 1 plasma samples. For Ref-Fab#5 comprising SEQ ID NO: 76 (EQ construct), induction of the expression of the cell surface marker is observable in presence of only 1 plasma sample. For Ref-Fab#6, none of the tested constructs comprising SEQ ID NO: 74 or 76 induced receptor activation in the presence of human plasma samples.

Figure 5:
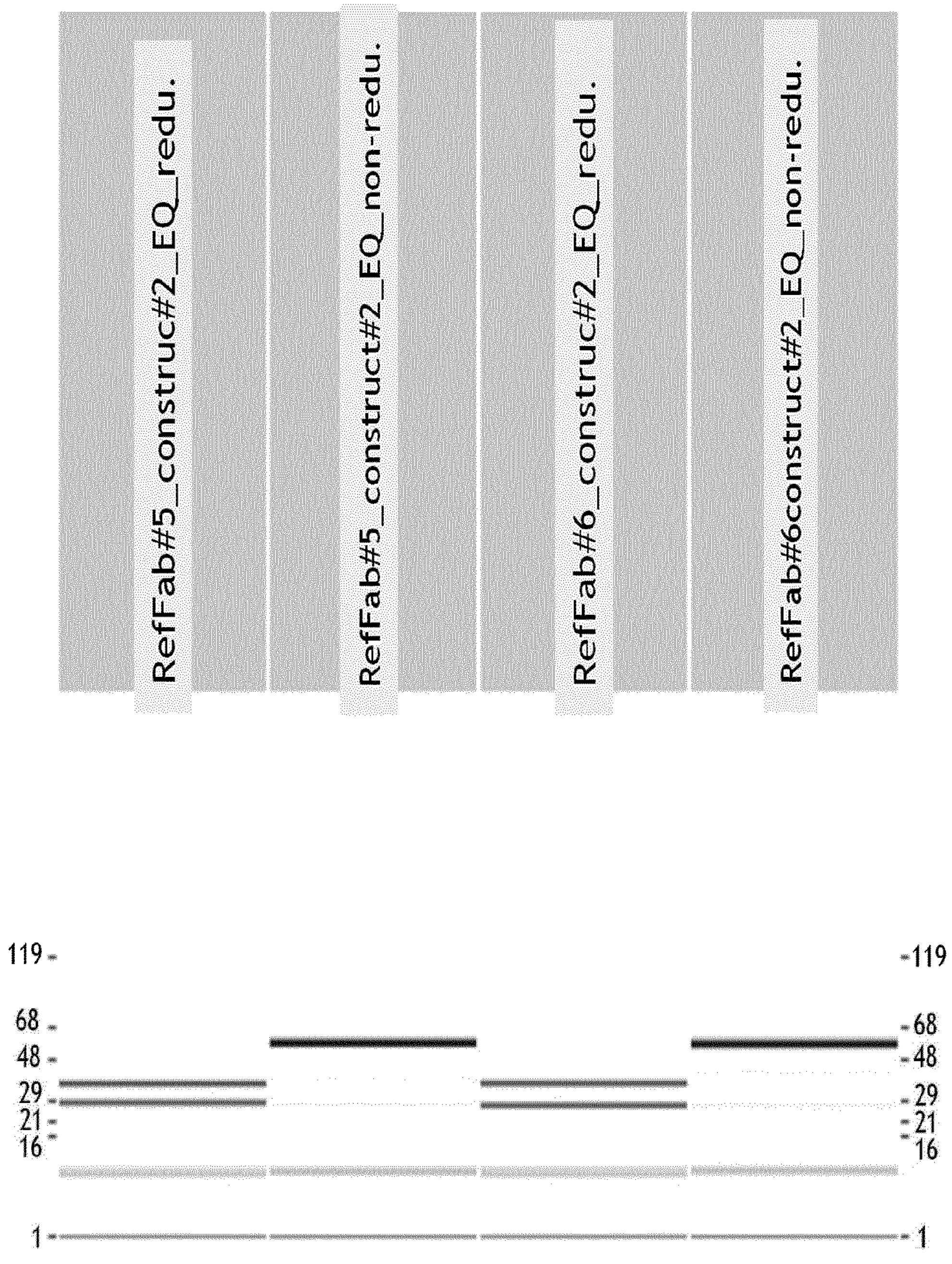

FIG. 5: SDS-PAGE of mammalian produced Ref-Fab#5 and Ref-Fab#6 bearing a modified heavy chain constant region comprising SEQ ID NO: 76, under reducing and non-reducing conditions. The two detectable protein bands under reducing conditions reflect the individual Fab heavy and light chains, whereas the single protein band detectable under non-reducing conditions reflect the whole Fab molecule. The results clearly confirmed disulfide-bridge formation between the light chain and the modified heavy chain for each of the Fabs.

FIG. 6: A) ELISA and B) Cell-ELISA binding of Ref-Fab#5 and Ref-Fab#6 bearing a modified heavy chain constant region comprising SEQ ID NO: 76 to Receptor-X. Both binding assays confirmed that a modified heavy chain constant region according to the present disclosure did not affected target binding.

Figure 7:
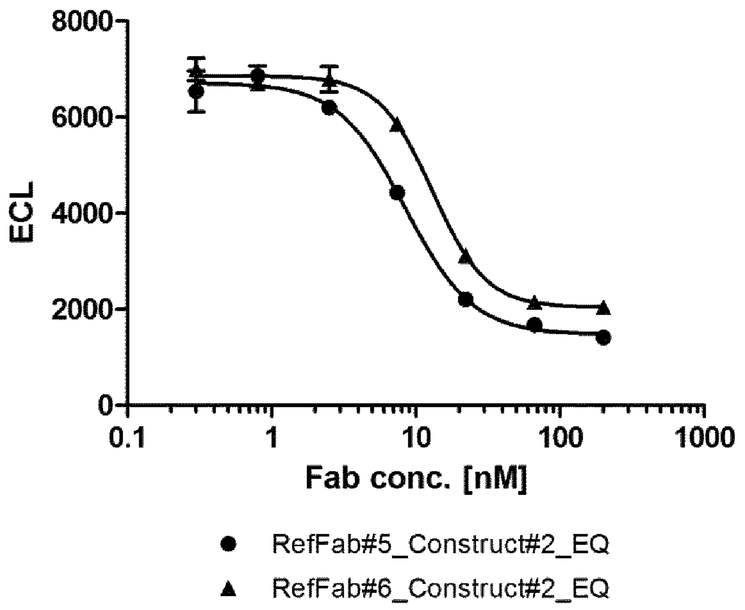

FIG. 7: MSD-based functional characterization of Ref-Fab#5 and Ref-Fab#6 bearing a modified heavy chain constant region comprising SEQ ID NO: 76 in a Receptor-X/ligand binding inhibition assay. Both Fabs significantly inhibited binding of the ligand to the receptor in a dose dependent manner. The assay confirmed that a modified heavy chain constant region according to the present disclosure did not affected the antagonistic activity of the Fab.

SUMMARY OF THE INVENTION

The present disclosure provides Fab molecules comprising a modified heavy chain constant region, wherein the modified heavy chain constant region prevents binding of pre-existing anti-Fab antibodies present in a host's serum to said Fab.

Specifically, the modified heavy chain constant region according to the present disclosure comprises one or more amino acid residues of a rodent (e.g., rat or mouse) IgG hinge region and a CH1 constant domain, wherein the CH1 constant domain is of a non-rodent IgG isotype (e.g., human IgG).

The Fab of the present disclosure does not induce target antigen activation through patient specific anti-human Fab antibodies. More specifically, the Fab of the present disclosure does not induce receptor activation through patient specific anti-Fab antibodies. Such a receptor may comprise, but are not limited to, receptor tyrosine kinases or glycoprotein receptors. In another aspect of the present disclosure, the Fab molecule of the present disclosure prevents signaling by anti-human Fab antibody induced receptor clustering.

The present disclosure also provides methods for preventing a Fab to be recognized by anti-Fab antibodies present in a host's serum consisting in preventing the formation of an epitope which is recognized by anti-Fab antibodies by replacing the hinge region of the Fab with a hinge region derived from a distinct species.

In particular, the inventors of the present disclosure identified that replacing the hinge region of a human Fab with one or more amino acid residues of a non-human hinge region (e.g., a rodent species), prevents the binding of anti-Fab antibodies present in human serum. In other words, the presence of the non-human hinge rendered the human Fab molecule less discernible by pre-existing anti-Fab antibodies present in human serum.

In an embodiment, the present disclosure provides a Fab comprising a modified heavy chain constant region, wherein the modified heavy chain constant region comprises a CH1 domain and one or more amino acids of a hinge region, wherein the hinge region is of a rodent IgG isotype and the CH1 domain is not of a rodent IgG isotype, and wherein said modified heavy chain constant region inhibits recognition of said Fab by anti-Fab antibodies present in serum.

In an embodiment, the present disclosure provides a Fab comprising a modified heavy chain constant region, wherein the rodent hinge region comprises the amino acid sequence of any one of SEQ ID NO: 16-21, 22-26, 27-34, 93, 35-36, 37-42, 43-47, 48-53, 54-58, 59-60, wherein X, X2, X3 are any amino acid residue except cysteine with the proviso that X2 and X3 constitute a sequence motif which is not DG, NG, NS.

In an embodiment, the present disclosure provides a Fab comprising a modified heavy chain constant region, wherein the rodent hinge region is of wildtype rat IgG2a (SEQ ID NO: 22) or rat IgG2b isotype (SEQ ID NO: 27), or comprises an amino acid sequence that is at least 80% identical to the amino acid sequence of a wildtype rat IgG2a or rat IgG2b hinge region.

In an embodiment, the present disclosure provides a Fab comprising a modified heavy chain constant region, wherein the rodent hinge region is of wildtype rat IgG2b isotype and comprises the amino acid sequence of any one of SEQ ID NO: 32-34, SEQ ID NO: 93, wherein X2, X3 are any amino acid residues except cysteine with the proviso that X2 and X3 constitute a sequence motif which is not DG, NG, NS.

In an embodiment, the present disclosure provides a Fab comprising a modified heavy chain constant region, wherein the rodent hinge region comprises the amino acid sequence ERRX2X3GIGHKC (SEQ ID NO: 33), wherein X2, X3 are any amino acid residues except cysteine with the proviso that X2 and X3 constitute a sequence motif which is not DG, NG, NS.

In an embodiment, the present disclosure provides a Fab comprising a modified heavy chain constant region, wherein the rodent hinge region comprises the amino acid sequence of any one of ERRNGGIGHKC (SEQ ID NO: 32), EERNGGIGHKC (SEQ ID NO: 93), ERRQGGIGHKC (SEQ ID NO: 34) or VPREC (SEQ ID NO: 26).

In an embodiment, the present disclosure provides a Fab comprising a modified heavy chain constant region, wherein the hinge region consists of the amino acid sequence of any one of ERRNGGIGHKC (SEQ ID NO: 32), EERNGGIGHKC (SEQ ID NO: 93), ERRQGGIGHKC (SEQ ID NO: 34), VPREC (SEQ ID NO: 26).

In an embodiment, the present disclosure provides a Fab comprising a modified heavy chain constant region, wherein the CH1 domain is a human IgG1 CH1 domain.

In an embodiment, the present disclosure provides a Fab comprising a modified heavy chain constant region, wherein the CH1 domain is a wildtype human IgG1 CH1 domain, any allotype of a wildtype human IgG1 CH1 domain or comprises an amino acid sequence that is at least 95% identical to the amino acid sequence of a wildtype human IgG1 CH1 domain.

In an embodiment, the present disclosure provides a Fab comprising a modified heavy chain constant region, wherein the CH1 domain comprises at least the amino acid sequence of any one of DKKV (SEQ ID NO: 86), DKRV (SEQ ID NO: 87), EKKV (SEQ ID NO: 88), DKKI (SEQ ID NO: 89), DKGV (SEQ ID NO: 90), DKEV (SEQ ID NO: 91) from position 212 to 215 (EU numbering).

In an embodiment, the present disclosure provides a Fab comprising a modified heavy chain constant region, wherein the CH1 domain comprises the amino acid sequence of any one of ASTKGPSVFPLAPSSKSTSGGTAALGCLVKDYFPEPVTVSWNSGALTSGVHTFPAVLQSSGLYSLSSWTVPSSSLGTQTYICNVNHKPSNTKVDKKV (SEQ ID NO: 1), ASTKGPSVFPLAPSSKSTSGGTAALGCLVKDYFPEPVTVSWNSGALTSGVHTFPAVLQSSGLYSLSSWTVPSSSLGTQTYICNVNHKPSNTKVDKRV (SEQ ID NO: 2), ASTKGPSVFPLAPSSKSTSGGTAALGCLVKDYFPEPVTVSWNSGALTSGVHTFPAVLQSSGLYSLSSWTVPSSSLGTQTYICNVNHKPSNTKVDKKI (SEQ ID NO: 7), ASTKGPSVFPLAPSSKSTSGGTAALGCLVKDYFPEPVTVSWNSGALTSGVHTFPAVLQSSGLYSLSSWTVPSSSLGTQTYICNVNHKPSNTKVEKKV (SEQ ID NO: 8), ASTKGPSVFPLAPSSKSTSGGTAALGCLVKDYFPEPVTVSWNSGALTSGVHTFPAVLQSSGLYSLSSWTVPSSSLGTQTYICNVNHKPSNTKVDKGV (SEQ ID NO: 9), ASTKGPSVFPLAPSSKSTSGGTAALGCLVKDYFPEPVTVSWNSGALTSGVHTFPAVLQSSGLYSLSSWTVPSSSLGTQTYICNVNHKPSNTKVDKEV (SEQ ID NO: 10) or an amino acid sequence that differs from SEQ ID NO 1, 2, 7, 8, 9, or 10 in at most 5 amino acids or is at least 95% identical to SEQ ID NO 1, 2, 7, 8, 9, or 10.

In an embodiment, the present disclosure provides a Fab comprising a modified heavy chain constant region, wherein the CH1 domain comprises the amino acid substitution D212E, K214G, K214E, R214G, R214G or V215I.

In an embodiment, the present disclosure provides a Fab comprising a modified heavy chain constant region, comprising a CH1 domain and one or more amino acid residues of a hinge region in order from N- to C-terminus, and wherein (a) the CH1 domain comprises an amino acid sequence of any one of SEQ ID NO: 1, SEQ ID NO: 2, SEQ ID NO: 7-10, or an amino acid sequence that differs therefrom in at most 5 amino acids or which is at least 95% identical to SEQ ID NO: 1, SEQ ID NO: 2, SEQ ID NO: 7-10, and (b) a hinge region comprising an amino acid sequence of any one of SEQ ID NO: 16-21, 22-26, 27-34, 93, 35-36, 37-42, 43-47, 48-53, 54-58, 59-60 or a sequence which differs therefrom in at most 5 amino acids and wherein X, X2, X3 are any amino acid residues except cysteine, with the proviso that X2 and X3 constitute a sequence motif which is not DG, NG or NS.

In an embodiment, the present disclosure provides a Fab comprising a modified heavy chain constant region, comprising a CH1 domain and one or more amino acid residues of a hinge region in order from N- to C-terminus, and wherein (a) the CH1 domain comprises an amino acid sequence of any one of SEQ ID NO: 1, SEQ ID NO: 2, SEQ ID NO: 7-10, or an amino acid sequence that differs therefrom in at most 5 amino acids or which is at least 95% identical to SEQ ID NO: 1, SEQ ID NO: 2, SEQ ID NO: 7-10, and (b) a hinge region comprising an amino acid sequence of any one of SEQ ID NO: 16-21, 22-26, 27-34, 93, 35-36 or a sequence which differs therefrom in at most 5 amino acids and wherein X, X2, X3 are any amino acid residues except cysteine, with the proviso that X2 and X3 constitute a sequence motif which is not DG, NG or NS.

In an embodiment, the present disclosure provides a Fab comprising a modified heavy chain constant region comprising an amino acid sequence selected from the group consisting of SEQ ID NO: 70-76.

In an embodiment, the present disclosure provides a Fab comprising a modified heavy chain constant region, comprising a CH1 domain and a hinge region in order from N- to C-terminus, and wherein (a) the CH1 domain consists of the amino acid sequence ASTKGPSVFPLAPSSKSTSGGTAALGCLVKDYFPEPVTVSWNSGALTSGVHTFPAVLQSSG LYSLSSWTVPSSSLGTQTYICNVNHKPSNTKVDKEV (SEQ ID NO: 10) and (b) the hinge region consists the amino acid sequence ERRQGGIGHKC (SEQ ID NO: 34).

In an embodiment, the present disclosure provides a Fab comprising a modified heavy chain constant region, comprising a CH1 domain and a hinge region in order from N- to C-terminus, and wherein (a) the CH1 domain comprises the amino acid sequence ASTKGPSVFPLAPSSKSTSGGTAALGCLVKDYFPEPVTVSWNSGALTSGVHTFPAVLQSSG LYSLSSWTVPSSSLGTQTYICNVNHKPSNTKVDKEV (SEQ ID NO: 10) and (b) the hinge region comprises the amino acid sequence ERRQGGIGHKC (SEQ ID NO: 34).

In an embodiment, the present disclosure provides a Fab comprising a modified heavy chain constant region, wherein the Fab binds specifically to a cell surface receptor.

In an embodiment, the present disclosure provides a Fab comprising a modified heavy chain constant region, wherein the Fab binds specifically to a cell surface receptor and prevents receptor activation through the presence of anti-Fab antibodies present in human serum.

In an embodiment, the present disclosure provides a method of preparing a Fab comprising a modified heavy chain constant region, wherein the Fab comprises a CH1 domain and a hinge region in order from N- to C-terminus, comprising the steps of:

(a) providing a Fab comprising a hinge that is not a rodent IgG hinge;

(b) replacing the hinge with one or more amino acid residues of a rodent hinge, respectively.

In an embodiment, the present disclosure provides a Fab obtainable by the methods disclosed herein.

In an embodiment, the present disclosure provides a method of preventing recognition of a Fab by anti-Fab antibodies present in serum comprising the step of:

(a) providing a Fab comprising a hinge region that is not a rodent IgG hinge;

(b) replacing the hinge with a rodent hinge, respectively.

In an embodiment, the present disclosure provides a method of treating a subject, comprising administering the Fab of the present disclosure.

In an embodiment, the present disclosure provides the use of a Fab according to the present disclosure of for the treatment of a disease.

In an embodiment, the present disclosure provides a recombinant nucleic acid molecule encoding the Fab of the present disclosure In an embodiment, the present disclosure provides a vector comprising the nucleic acid encoding the Fab of the present disclosure.

In an embodiment, the present disclosure provides a recombinant host cell comprising the nucleic acid molecule encoding the Fab of the present disclosure.

In an embodiment, the present disclosure provides a pharmaceutical composition comprising a Fab of the present disclosure and a pharmaceutically acceptable carrier or excipient.

An aspect of the present disclosure relates to the use of said pharmaceutical composition for the treatment of a disorder or condition associated with the undesired presence of a target antigen.

In an embodiment of the present disclosure, the Fab comprising a modified heavy chain constant region is a monoclonal Fab.

In an embodiment of the present disclosure, the Fab comprising a modified heavy chain constant region is an isolated Fab.

An aspect of the present disclosure pertains to the medical use of the disclosed Fab comprising a modified heavy chain constant region.

An aspect of the disclosure pertains to the use of the Fab comprising a modified heavy chain constant region for the treatment of cardiovascular disorder, inflammatory disorder or cancer in humans.

In an embodiment the Fab comprising a modified heavy chain constant region is a recombinant antibody.

The Fabs of the present disclosure fully retain their in vitro and ex vivo. Furthermore, the Fab molecules reveal excellent production properties in mammalian cell culture with no need to adapt existing purification protocols for human Fab molecules.

The present disclosure enables the use of Fabs as therapeutic proteins in which the target biology prevents the use of bivalent molecules and where it is therefore strictly required to employ monovalent molecules. Thus, the present disclosure enables a safe treatment for patients and avoids patient specific pharmacokinetic and pharmacodynamics variability.

Definitions

The terms "comprising", "comprises", "comprise" and "comprised of" as used herein are synonymous with "including", "includes" or "containing", "contains", and are inclusive or open-ended and do not exclude additional, non-recited members, elements or method steps.

By the term "peptide" is meant a short molecule having less than or equal to 93 amino acids.

The term "polypeptide" means a molecule having more than 93 amino acids.

The term "antibody" as used herein refers to a protein comprising at least two heavy (H) chains and two light (L) chains inter-connected by disulfide bonds which interacts (e.g., by binding, steric hindrance, stabilizing spatial distribution) with an antigen. Each heavy chain is comprised of a heavy chain variable region (abbreviated herein as VH) and a heavy chain constant region. The heavy chain constant region is comprised of 3 domains, CH1, CH2 and CH3 and the hinge region which connects the CH1 and CH2 domain. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies and chimeric antibodies. The antibodies can be of any isotype.

As used herein, "isotype" refers to the antibody class (e.g., IgG1, IgG2, IgG3, IgG4, IgM, IgA1, IgA2, IgD, and IgE antibody) that is encoded by the heavy chain constant domain genes. The full-length amino acid sequence of each wild type human IgG constant region (including all domains, i.e., CH1 domain, hinge, CH2 domain, and CH3 domain) is cataloged in the UniProt database available on-line, e.g., as P01857 (IgG1), P01859 (IgG2), P01860 (IgG3), and P01861 (IgG4), or different allotypes thereof. As used herein, a domain of a heavy chain constant region, e.g., the hinge, is of an "IgG1 isotype," "IgG2 isotype," "IgG3 isotype," or "IgG4 isotype," if the domain comprises the amino acid sequence of the corresponding domain of the respective isotype, or a variant thereof (that has a higher homology to the corresponding domain of the respective isotype than it does to that of the other isotypes).

A "wildtype" protein or portion thereof is a version of the protein as it is found in nature. An amino acid sequence of a wildtype protein, e.g., a heavy chain constant region, is the amino acid sequence of the protein as it occurs in nature. Due to allotypic differences, there can be more than one amino acid sequence for a wildtype protein. For example, there are several allotypes of naturally occurring human IGg1 heavy chain constant regions (see, e.g., Jeffries et al. (2009) mAbs 1:1).

"Allotype" refers to naturally occurring variants within a specific isotype group, which variants differ in a few amino acids (see, e.g., Jefferies et al. (2009) mAbs 1:1). Antibodies described herein may be of any allotype.

As used herein, the term "Fab molecule" or "Fab" corresponds to the light chain (LC) plus parts of the heavy chain (HC) of an immunoglobulin. More specifically, a Fab comprises a VL, VH, CL, CH1 domains and additionally parts of the hinge region of an immunoglobulin. Fabs may be produced either by proteolytic cleavage of IgG molecules or made through expression of recombinant molecules. Usually parts of the constant domain of the heavy chain (Fc part) are removed.

As used herein, a $F(ab)_2$ fragment is a molecule which comprises two Fab molecules linked by one or more disulfide bridges between the hinge regions of the two Fabs.

As used herein, the term "Fab heavy chain constant region" is meant to refer to an amino acid sequence comprising the CH1 domain and the parts of the hinge region of an IgG molecule.

A "hinge", "hinge domain" or "hinge region" or "IgG hinge region" refers to the domain of a heavy chain constant region that joins the CH1 domain to the CH2 domain. The hinge provides varying levels of flexibility between the binding and effector regions of an antibody and also provides sites for intermolecular disulfide bonding between the two heavy chain constant regions. As used herein, a full human IgG1, IgG2, and IgG4 hinge starts at E216 (EU numbering) and ends at G230 (EU numbering). A human IgG3 H1 hinge region starts at E 216 and ends at R 228 (see IMGT http://www.imgt.org/IMGTScientificChart/Numbering/Hu_IGHGnber.html). The sequences of various human, rat and mouse hinges are depicted in Table 1-3. The term "hinge" includes wildtype hinges as well as variants thereof (e.g., non-naturally-occurring hinges or modified hinges).

For example, the term "rat IgG2b hinge" includes wildtype rat IgG2b hinge (SEQ ID: 27 (Table 1), and variants having 1, 2, 3, 4, 5, 6, 7, 8, 9, 10, 11, 12, 13, 14, 15, 16, 17, 18, 19, 20, 21, 1-2, 1-3, 1-5, 3-5, 1-10, 3-10, 5-10, 1-21, 5-21, 10-21 and/or at most 21, 15, 12, 10, 9, 8, 7, 6, 5, 4, 3, 2, or 1 mutations, e.g., substitutions, deletions or additions.

Exemplary rat IgG2b hinge variants according to the present disclosure may include hinges in which 3 of the 4 present cysteines (C11, C14, C17, C20 according Table 1) are changed to another amino acid and wherein 1 cysteine is maintained to allow disulfide bond formation between the modified heavy chain constant region and the light chain constant region of the Fab. Other exemplary rat IgG2b hinge variants of the present disclosure includes hinges in which the sequence motif "NG" (position 4-5 according Table 1) is substituted with any other sequence motif with does not constitutes a potential posttranslational modification site. Such potential posttranslational modification sites may include amongst others, "DG", "NG", "NS", sequence motifs. Preferably, the substitution sequence consists of a "QG" motif.

Exemplary rat and mouse hinge sequences used in the modified heavy chain constant region of the present disclosure are depicted in Table 1 and Table 2, respectively.

Preferred hinge sequences present in the modified heavy chain constant regions of the present disclosure consists of the sequences selected from the group consisting of SEQ ID NO: 26, SEQ ID NO: 32-34 or SEQ ID NO: 93.

TABLE 1

X, X2, X3 indicate any amino acid residue except cysteine. X2 and X3 may constitute any sequence motif which is not DG, NG or NS

| Hinge description/ | Amino acid sequence | | | | | | | | | | | | | | | | | | | | | SEQ ID |
|---|---|---|---|---|---|---|---|---|---|---|---|---|---|---|---|---|---|---|---|---|---|---|
| Relative Hinge Position | 1 | 2 | 3 | 4 | 5 | 6 | 7 | 8 | 9 | 10 | 11 | 12 | 13 | 14 | 15 | 16 | 17 | 18 | 19 | 20 | 21 | NO:: |
| wt rat IgG1 | V | P | R | N | **C** | G | G | D | **C** | K | P | **C** | I | **C** | T | | | | | | | 16 |
| wt rat IgG1 with C5X, C9X, C12X | V | P | R | N | **X** | G | G | D | **X** | K | P | **X** | I | **C** | T | | | | | | | 17 |
| wt rat IgG1 with C5X, C9X, C14X | V | P | R | N | **X** | G | G | D | **X** | K | P | **C** | I | **X** | T | | | | | | | 18 |
| wt rat IgG1 with C5X, C12X, C14X | V | P | R | N | **X** | G | G | D | **C** | K | P | **X** | I | **X** | T | | | | | | | 19 |
| wt rat IgG1 with C9X, C12X, C14X | V | P | R | N | **C** | G | G | D | **X** | K | P | **X** | I | **X** | T | | | | | | | 20 |

TABLE 1-continued

X, X2, X3 indicate any amino acid residue except cysteine. X2 and X3 may constitute any sequence motif which is not DG, NG or NS

| Hinge description/ Relative Hinge Position | 1 | 2 | 3 | 4 | 5 | 6 | 7 | 8 | 9 | 10 | 11 | 12 | 13 | 14 | 15 | 16 | 17 | 18 | 19 | 20 | 21 | SEQ ID NO:: |
|---|---|---|---|---|---|---|---|---|---|---|---|---|---|---|---|---|---|---|---|---|---|---|
| truncated wt rat IgG1 | V | P | R | N | **C** | | | | | | | | | | | | | | | | | 21 |
| wt rat IgG2a | V | P | R | E | **C** | N | P | **C** | G | **C** | T | | | | | | | | | | | 22 |
| wt rat IgG2a with C8X, C10X | V | P | R | E | **C** | N | P | **X** | G | **X** | T | | | | | | | | | | | 23 |
| wt rat IgG2a with C5X, C10X | V | P | R | E | **X** | N | P | **C** | G | **X** | T | | | | | | | | | | | 24 |
| wt rat IgG2a with C5X, C8X | V | P | R | E | **X** | N | P | **X** | G | **C** | T | | | | | | | | | | | 25 |
| truncated wt rat IgG2a | V | P | R | E | **C** | | | | | | | | | | | | | | | | | 26 |
| wt rat IgG2b | E | R | R | N | G | G | I | G | H | K | **C** | P | T | **C** | P | T | **C** | H | K | **C** | P | 27 |
| wt rat IgG2b with C14X, C17X, C20X | E | R | R | N | G | G | I | G | H | K | **C** | P | T | **X** | P | T | **X** | H | K | **X** | P | 28 |
| wt rat IgG2b with C11X, C17X, C20X | E | R | R | N | G | G | I | G | H | K | **X** | P | T | **C** | P | T | **X** | H | K | **X** | P | 29 |
| wt rat IgG2b with C11X, C14X, C20X | E | R | R | N | G | G | I | G | H | K | **X** | P | T | **C** | P | T | **X** | H | K | **X** | P | 30 |
| wt rat IgG2b with C11X, C14X, C27X | E | R | R | N | G | G | I | G | H | K | **X** | P | T | **X** | P | T | **X** | H | K | **C** | P | 31 |
| truncated wt rat IgG2b | E | R | R | N | G | G | I | G | H | K | **C** | | | | | | | | | | | 32 |
| truncated wt rat IgG2b with R3E | E | **E** | R | N | G | G | I | G | H | K | **C** | | | | | | | | | | | 32 |
| truncated wt rat IgG2b with N4X2 and G5X3 | E | R | R | **X2** | **X3** | G | I | G | H | K | **C** | | | | | | | | | | | 33 |
| truncated wt rat IgG2b with N4Q | E | R | R | **Q** | **G** | G | I | G | H | K | **C** | | | | | | | | | | | 34 |
| wt rat IgG2c | E | P | R | R | P | K | P | R | P | P | T | D | **I** | **C** | S | | | | | | | 35 |
| truncated wt rat IgG2c | E | P | R | R | P | K | P | R | P | P | T | D | **I** | **C** | | | | | | | | 36 |

TABLE 2

X indicates any amino acid residue cysteine

| Hinge description/ Relative Hinge Position | 1 | 2 | 3 | 4 | 5 | 6 | 7 | 8 | 9 | 10 | 11 | 12 | 13 | 14 | 15 | 16 | 17 | 18 | 19 | 20 | 21 | 21 | SEQ ID NO: |
|---|---|---|---|---|---|---|---|---|---|---|---|---|---|---|---|---|---|---|---|---|---|---|---|
| wt mouse IgG1 | V | P | R | D | **C** | G | **C** | K | P | **C** | I | **C** | T | | | | | | | | | | 37 |
| wt mouse IgG1 with C5X, C9X, C12X | V | P | R | D | **X** | G | **X** | K | P | **X** | I | **C** | T | | | | | | | | | | 38 |
| wt mouse IgG1 with C7X, C10X, C12X | V | P | R | D | **C** | G | **X** | K | P | **X** | I | **X** | T | | | | | | | | | | 39 |
| wt mouse IgG1 with C5X, C10X, C14X | V | P | R | D | **X** | G | **C** | K | P | **X** | I | **X** | T | | | | | | | | | | 40 |
| wt mouse IgG1 with C5X, C9X, C14X | V | P | R | D | **X** | G | **X** | K | P | **C** | I | **X** | T | | | | | | | | | | 41 |
| truncated wt mouse IgG1 | V | P | R | D | **C** | | | | | | | | | | | | | | | | | | 42 |

TABLE 2-continued

| X indicates any amino acid residue cysteine | | | | | | | | | | | | | | | | | | | | | | | |
|---|---|---|---|---|---|---|---|---|---|---|---|---|---|---|---|---|---|---|---|---|---|---|---|
| Hinge description/ | Amino acid sequence | | | | | | | | | | | | | | | | | | | | | | SEQ ID |
| Relative Hinge Position | 1 | 2 | 3 | 4 | 5 | 6 | 7 | 8 | 9 | 10 | 11 | 12 | 13 | 14 | 15 | 16 | 17 | 18 | 19 | 20 | 21 | 21 | NO: |
| wt mouse IgG2a | E | P | R | G | P | T | I | K | P | **C** | P | P | **C** | K | **C** | P | | | | | | | 43 |
| wt mouse IgG2a with C13, C15 | E | P | R | G | P | T | I | K | P | **C** | P | P | **X** | K | **X** | P | | | | | | | 44 |
| wt mouse IgG2a with C10, C15 | E | P | R | G | P | T | I | K | P | **X** | P | P | **C** | K | **X** | P | | | | | | | 45 |
| wt mouse IgG2a with C10, C13 | E | P | R | G | P | T | I | K | P | **X** | P | P | **X** | K | **C** | P | | | | | | | 46 |
| truncated wt mouse IgG2a | E | P | R | G | P | T | I | K | P | **C** | | | | | | | | | | | | | 47 |
| wt mouse IgG2b | E | P | S | G | P | I | S | T | I | N | P | **C** | P | P | **C** | K | E | **C** | H | K | **C** | P | 48 |
| wt mouse IgG2a with C15X, C18X, C21X | E | P | S | G | P | I | S | T | I | N | P | **C** | P | P | **X** | K | E | **X** | H | K | **X** | P | 49 |
| wt mouse IgG2a with C12X, C18X, C21X | E | P | S | G | P | I | S | T | I | N | P | **X** | P | P | **C** | K | E | **X** | H | K | **X** | P | 50 |
| wt mouse IgG2a with C12X, C15X, C21X | E | P | S | G | P | I | S | T | I | N | P | **X** | P | P | **X** | K | E | **C** | H | K | **X** | P | 51 |
| wt mouse IgG2a with C12X, C15X, C18X | E | P | S | G | P | I | S | T | I | N | P | **X** | P | P | **X** | K | E | **X** | H | K | **C** | P | 52 |
| truncated wt mouse IgG2b | E | P | S | G | P | I | S | T | I | N | P | **C** | | | | | | | | | | | 53 |
| wt mouse IgG2c | E | P | R | V | P | I | T | Q | N | P | **C** | P | P | L | K | E | **C** | P | P | **C** | A | | 54 |
| wt mouse IgG2c with C17X, C20X | E | P | R | V | P | I | T | Q | N | P | **C** | P | P | L | K | E | **X** | P | P | **X** | A | | 55 |
| wt mouse IgG2c with C11X, C20X | E | P | R | V | P | I | T | Q | N | P | **X** | P | P | L | K | E | **C** | P | P | **X** | A | | 56 |
| wt mouse IgG2c with C11X, C17X | E | P | R | V | P | I | T | Q | N | P | **X** | P | P | L | K | E | **X** | P | P | **C** | A | | 57 |
| truncated wt mouse IgG2c | E | P | R | V | P | I | T | Q | N | P | **C** | | | | | | | | | | | | 58 |
| wt mouse IgG3 | E | P | R | I | P | K | P | S | T | P | P | G | S | S | **C** | P | | | | | | | 59 |
| truncated wt mouse IgG3 | E | P | R | I | P | K | P | S | T | P | P | G | S | S | **C** | | | | | | | | 60 |

The hinge region may also be a chimeric hinge that comprises sequences from at least two species. For example, a hinge may comprise one or more amino acid residues from one species (e.g., rat) and the remainder of the hinge region comprises one or more amino acid residues from other species (e.g., mouse).

The hinge region may also comprise sequences from at least two IgG isotypes (e.g., IgG1 and IgG2). For example, a hinge according to the present disclosure may comprise one or more amino acid residues from a rat IgG2a isotype and one or more amino acid residues from a rat IgG2b isotype.

A "non-rodent IgG" hinge refers to a hinge that is not of a rat or mouse IgG isotype.

The term "CH1 domain" refers to the heavy chain constant domain of an antibody linking the variable domain to the hinge in a heavy chain constant domain. As used herein, a human IgG CH1 domain starts at EU position A118 and ends at EU position V215. The term "CH1 domain" also includes wildtype human CH1 domains (such as having SEQ ID NO: 1 for human IgG1 and one of its natural occurring allotypes (such as having SEQ ID NO: 2); SEQ ID NO: 3 for IgG2; SEQ ID NO: 4 for IgG3 or SEQ ID NO: 5 for IgG4), as well as variants thereof (e.g., non-naturally-occurring CH1 domains or modified CH1 domains).

For example, the term "CH1 domain" includes wildtype human CH1 domains and variants thereof having 1, 2, 3, 4, 5, 1-3, 1-5, 3-5 and/or at most 5, 4, 3, 2, or 1 mutations, e.g., substitutions, deletions or additions.

Exemplary human CH1 constant domains according to the present disclosure includes CH1 domains, in which 1, 2, 3, or 4 amino acid residues at the C-terminal end of the CH1 domain (EU position 212-215 or EU position D212, K213, K214 or R214, V215) are changed to another naturally occurring amino acid except cysteine. Preferably, the substitutions includes not more than one amino acid exchange. Preferably, the substitution consists of D212E, K214G or K214E, R214G or R214G, or V215I.

Table 3 provides a listing of the different amino acid sequences of the human CH1 and hinge regions of various IgG subclasses and variants thereof.

TABLE 3

| Antibody Class | CH1 or hinge region | Seq ID |
|---|---|---|
| Wt human IgG1 CH1 | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKV | 1 |
| human IgG1 (natural allotype) CH1 | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDK**R**V | 2 |
| Wt human IgG1 CH1 with variant postions 212, 214, 215 | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKV**XKXX** | 6 |
| Wt human IgG1 CH1 with V215I | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKV**DKKI** | 7 |
| Wt human IgG1 CH1 with D212E | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKV**EKKV** | 8 |
| Wt human IgG1 CH1 with K214G | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKV**DKGV** | 9 |
| Wt human IgG1 CH1 with K214E | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKV**DKEV** | 10 |
| Wt Human IgG1 hinge | **EPKSCDKTHTCPPCP** | 11 |
| Wt Human IgG1 hinge truncated | **EPKSC** | 94 |
| Wt Human IgG2 | ASTKGPSVFPLAPCSRSTSESTAALGCLVKDYFPEPVTVSWNSGALTSGVHTFPA VLQSSGLYSLSSVVTVPSSNFGTQTYTCNVDHKPSNTKVDKTV | 3 |
| Wt Human IgG2 hinge | **ERKCCVECPPCP** | 12 |
| Wt human IgG3 | ASTKGPSVFPLAPCSRSTSGGTAALGCLVKDYFPEPVTVSWNSGALTSGVHTFPA VLQSSGLYSLSSVVTVPSSSLGTQTYTCNVNHKPSNTKVDKRV | 4 |
| human IgG3 hinge (H1) | **ELKTPLGDTTHTCPRCP** | 13 |
| Wt human IgG3 hinge (natural variant) | **EPKSCDTPPPCPRCP** | 14 |
| Wt human IgG4 | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRV | 5 |
| Wt human IgG4 hinge | **ESKYGPPCPSCP** | 15 |

The term "modified heavy chain constant region" is defined herein as a molecule which has the CH1 domain derived from an antibody of one species (e.g. human IgG) and one more amino acids of a hinge region of an antibody of a different species (e.g. rat IgG). The hinge region of the different species removes the epitope present in the originating hinge region which is recognized by anti-Fab antibodies present in serum. Preferably, the CH1 domain is derived from sequences found in humans, e.g. in the human germline or somatic cells, and the hinge region is derived from sequences found in a non-human animal, e.g. a mouse or rat.

As used herein, "engineered Fab" or "modified Fab" refers to a Fab molecule that has been genetically engineered to contain an modified heavy chain constant region wherein one or more amino acid residues of the parental hinge region at the C-terminus of the Fab heavy chain. The exchange causes that the previously present epitope recognized by anti-Fab antibodies is removed and thus prevents recognition and binding of the Fab to anti-Fab antibodies.

An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody. By engineering or modify an antibody improved variants of the parental clone can be achieved. Meanwhile various technologies e.g. to improve the affinity, to reduce immunogenicity and to increase the effector function of an antibody are established in the art.

The term "epitope" includes any proteinacious region which is specifically recognized by an antibody or fragment thereof or a T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope. An epitope can comprise those residues to which the antibody binds and may be "linear" or "conformational." The term "linear epitope" refers to an epitope wherein all of the points of interaction between the protein and the interacting molecule (such as an antibody) occur linearly along the primary amino acid sequence of the protein (continuous). The term "conformational epitope" refers to an epitope in which discontinuous amino acids that come together in three dimensional conformations. In a conformational epitope, the points of interaction occur across amino acid residues on the protein that are separated from one another. For example, an epitope can be one or more amino acids within a stretch of amino acids as shown by peptide mapping or HDX, or one or more individual amino acids as shown by X-ray crystallography.

The term "isolated" refers to a compound which can be e.g. an antibody or antibody fragment that is substantially free of other antibodies or antibody fragments having different antigenic specificities. Moreover, an isolated antibody or antibody fragment may be substantially free of other cellular material and/or chemicals. Thus, in some aspects, antibodies provided are isolated antibodies which have been separated from antibodies with a different specificity. An isolated antibody may be a monoclonal antibody. An isolated antibody may be a recombinant monoclonal antibody. An isolated antibody that specifically binds to an epitope, isoform or variant of a target may, however, have cross-reactivity to other related antigens, e.g., from other species (e.g., species homologs).

The term "monoclonal antibody" as used herein refers to a preparation of antibody molecules of single molecular composition. A monoclonal antibody composition displays a unique binding site having a unique binding specificity and affinity for particular epitopes.

As used herein, an antibody "binds specifically to", "specifically binds to", is "specific to/for" or "specifically recognizes" an antigen if such antibody is able to discriminate between such antigen and one or more reference antigen(s), since binding specificity is not an absolute, but a relative property. The reference antigen(s) may be one or more closely related antigen(s), which are used as reference points. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. Additionally, "specific binding" may relate to the ability of an antibody to discriminate between different parts of its target antigen, e.g. different domains or regions or between one or more key amino acid residues or stretches of amino acid residues.

As used herein, the term "affinity" refers to the strength of interaction between the polypeptide and its target at a single site. Within each site, the binding region of the polypeptide interacts through weak non-covalent forces with its target at numerous sites; the more interactions, the stronger the affinity.

As used herein, the term "pre-immunity" antibodies or "pre-existing" antibodies is meant to refer to antibodies that are normally present in an individual or organism.

As used herein, the term "antigenic" refers to the ability of a compound to react with the immune system, i.e. antibodies.

As used herein, the terms "auto-antigenic sequence", "auto-antigenic peptide" are used interchangeably and are meant to refer to an amino acid sequence that is an epitope recognized by pre-immunity antibodies.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Typical host cells are prokaryotic (such as bacterial, including but not limited to *E. coli*) or eukaryotic (which includes yeast, mammalian cells, and more). Bacterial cells are preferred prokaryotic host cells and typically are a strain of *Escherichia coli* (*E. coli*) such as, for example, the *E. coli* strain DH5 available from Bethesda Research Laboratories, Inc., Bethesda, Md. Preferred eukaryotic host cells include yeast and mammalian cells including murine and rodents, preferably vertebrate cells such as those from a mouse, rat, monkey or human cell line, for example HKB11 cells, PERC.6 cells, or CHO cells.

As used herein, amino acid residues will be indicated either by their full name or according to the standard three-letter or one-letter amino acid code. "Natural occurring amino acids" means the following amino acids:

TABLE 1

| Amino acids | | |
|---|---|---|
| Amino acid | Three letter code | One letter code |
| Alanine | Ala | A |
| Arginine | Arg | R |
| Asparagine | Asn | N |
| Aspartic acid | Asp | D |

TABLE 1-continued

| Amino acids | | |
|---|---|---|
| Amino acid | Three letter code | One letter code |
| Cysteine | Cys | C |
| Glutamic acid | Glu | E |
| glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acid numbering is according EU numbering (Edelman, G. M. et al., Proc. Natl. Acad. USA, 63, 78-85 (1969). PMID: 5257969 and as depicted under http://www.imgt.org/IMGTScientificChart/Numbering/Hu_IGHGnber.html.

DETAILED DESCRIPTION OF THE INVENTION

The invention is based on the findings that the substitution of the hinge region of Fab with a hinge region derived from a different species (e.g. rodent IgG hinge) removes an epitope which is recognized by pre-existing anti-Fab antibodies present in a host's serum. Accordingly, the presence of the hinge region from a different species prevents the binding of pre-existing anti-Fab antibodies to said Fab. It may also prevent formation of anti-Fab/Fab complexes which may restore an undesired bivalent binding of full IgGs to their target antigen.

Accordingly, the present disclosure provides a Fab comprising a modified heavy chain constant region. More specifically, the present disclosure provides a Fab which comprise a light chain and a heavy chain, wherein one or more amino acid residues at the C-terminal end of the heavy chain are exchanged. More specifically, the modified heavy chain constant region encompasses a human CH1 domain and one or more amino acids of a hinge region derived from a different species. More specifically, the Fab of the present disclosure comprises a human CH1 domain and one or more amino acids of a rodent IgG hinge region (e.g., rat or mouse IgG).

The hinge region of a Fab comprising an unmodified heavy chain constant domain (e.g. human CH1+human hinge) is thought to comprise an auto-antigenic sequence which is a sequence capable of forming an epitope which is recognized by pre-existing anti-Fab antibodies present in a host. In contrast, the hinge region of a distinct species may constitute a non-auto-antigenic sequence when introduced into the Fab and thus is not recognized by pre-existing anti-Fab antibodies. Accordingly, the substitution of the hinge region of a Fab which comprises an auto-antigenic sequence with a hinge region from a different species causes that the previously present epitope which is recognized by anti-Fab antibodies present in a host's serum, is removed.

A modified heavy chain constant region according to the present disclosure may comprise a wildtype CH1 and a wildtype hinge region, or a variant thereof, e.g., a CH1 and hinge region having one or more amino acid substitutions, deletions or additions relative to the corresponding wildtype domain/region, and/or having an amino acid sequence that is at least 90% identical, or more, to the corresponding wildtype sequence.

In an embodiment, the present disclosure provides a Fab comprising a modified heavy chain constant region, wherein said modified heavy chain constant region comprises a CH1 domain and one or more amino acids of a hinge region, wherein the hinge region is of rodent IgG isotype and the CH1 domain is not of a non-rodent IgG isotype.

In an embodiment, the present disclosure provides a Fab comprising a modified heavy chain constant region, wherein said modified heavy chain constant region comprises a CH1 domain and one or more amino acids of a hinge region, wherein the hinge region is of a rodent IgG isotype and the CH1 domain is not of a non-rodent IgG isotype, and wherein said modified heavy chain constant region inhibits recognition of said Fab by anti-Fab antibodies present in serum.

Exemplary modified heavy chain constant regions include one or more amino acid residues of a rodent (e.g., rat or mouse) hinge region and a CH1 domain, wherein the CH1 domain is not of the rodent IgG isotype and may be, e.g., of a human IgG1, IgG2, IgG3 or IgG4 isotype.

In certain embodiments, the modified heavy chain constant region comprises one or more amino acids of a rat IgG2a or rat IgG2b hinge region and a CH1 domain.

In certain embodiments, the modified heavy chain constant region comprises one or more amino acids of a rat IgG2a hinge region and a CH1 constant domain.

In certain embodiments, the modified heavy chain constant region comprises one or more amino acids of a rat IgG2b hinge region and a CH1 domain.

In certain embodiments, the modified heavy chain constant region comprises a human IgG1 CH1 constant domain.

In certain embodiments, the modified heavy chain constant region comprises a human IgG1 CH1 constant domain or variant thereof.

In certain embodiments, the modified heavy chain constant region comprises one or more amino acids of a rat IgG2a or rat IgG2b hinge region and a CH1 domain, wherein the CH1 domain is not a wild-type rat IgG2a or rat IgG2b constant region or variant thereof.

In certain embodiments, the modified heavy chain constant region comprises one or more amino acids of a rat IgG2a or rat IgG2b hinge region and a CH1 domain, wherein the CH1 domain is a human IgG constant region or variant thereof.

In certain embodiments, the modified heavy chain constant region comprises one or more amino acids of a rat IgG2a or rat IgG2b hinge region and a CH1 domain, wherein the CH1 domain consists of a human IgG1 constant domain or variant thereof.

In certain embodiments, the modified heavy chain constant region comprises one or more amino acids of a rat IgG2b hinge region and a CH1 domain, wherein the CH1 domain is a human IgG1 constant region or variant thereof.

The modified heavy chain constant region of the present disclosure can include the corresponding wildtype amino acid sequence, or a variant thereof, e.g., one or more (e.g., between 1-10, or more) amino acid substitutions or deletions within the hinge and/or the CH1 domain relative to the wildtype amino acid sequence. Accordingly, the amino acid sequence of the hinge and/or the CH1 domain is at least about 80%, 85%, 90%, 95%, or more (i.e., 96%, 97%, 98%, 99%, or 100%) identical to the corresponding wildtype amino acid sequence.

Generally, variants of the CH1 or hinge region may comprise 1, 2, 3, 4, 5, 6, 7, 8, 9, 10 or more mutations, and/or at most 10, 9, 8, 7, 6, 5, 4, 3, 2 or 1 mutation, or 1-10 or 1-5 mutations, or comprise an amino acid sequence that is at least about 75%, 80%, 85%, 90%, 95%, 96%, 97%, 98%, or 99% identical to that of the corresponding wildtype domain (CH1, or hinge, respectively), provided that the heavy chain constant region comprising the specific variant retains the necessary biological activity.

In an embodiment, the present disclosure provides a Fab comprising a modified heavy chain constant region, wherein said modified heavy chain constant region inhibits recognition of said Fab by anti-Fab antibodies present in human serum.

CH1 Constant Domain

The modified heavy chain constant domain of the present disclosure may comprise a human IgG1 CH1 domain that is wildtype or variant; a human IgG2 CH1 domain that is wildtype or variant, a human IgG3 CH1 domain that is wildtype or variant or a human IgG4 CH1 domain that is wildtype or variant.

In an embodiment, the present disclosure provides a Fab comprising a modified heavy chain constant region, wherein the CH1 domain is a human IgG1 CH1 domain.

In an embodiment, the present disclosure provides a Fab comprising a modified heavy chain constant region, wherein the CH1 domain is a wildtype human IgG1 CH1 domain or an amino acid sequence that is at least 95% identical to the amino acid sequence of a wildtype human IgG1 CH1 domain (SEQ ID NO: 1).

In an embodiment, the present disclosure provides a Fab comprising a modified heavy chain constant region, wherein the CH1 domain is a wildtype human IgG1 CH1 domain (SEQ ID NO: 1), any allotype of a wildtype human IgG1 CH1 domain or comprises an amino acid sequence that is at least 95% identical to the amino acid sequence of a wildtype human IgG1 CH1 domain (SEQ ID NO: 1).

In an embodiment, the present disclosure provides a Fab comprising a modified heavy chain constant region, wherein the CH1 domain comprises at least the amino acid sequence XKXX (SEQ ID NO: 92) from position 212 to 215 (EU numbering), wherein X is any amino acid residues except cysteine.

In an embodiment, the present disclosure provides a Fab comprising a modified heavy chain constant region, wherein the CH1 domain comprises at least the amino acid sequence of any one of DKKV (SEQ ID NO: 86), DKRV (SEQ ID NO: 87), EKKV (SEQ ID NO: 88), DKKI (SEQ ID NO: 89), DKGV (SEQ ID NO: 90), DKEV (SEQ ID NO: 91) from position 212 to 215 (EU numbering).

In an embodiment, the present disclosure provides a Fab comprising a modified heavy chain constant region, wherein the human CH1 domain comprises the amino acid substitution D212E, K214G, K214E, R214G, R214G or V215I.

In an embodiment, the present disclosure provides a Fab comprising a modified heavy chain constant region, wherein the CH1 domain comprises the amino acid sequence ASTKGPSVFPLAPSSKSTSGGTAALGCLVKDYFPEPVTVSWNSGALTSGVHTFPAVLQSSG LYSLSSWTVPSSSLGTQTYICNVNHKPSNTKVXKXX (SEQ ID NO: 6), wherein X is any amino acid residues except cysteine.

In certain embodiments, the CH1 domain is an allotype of the wildtype IgG1 CH1 domain having the amino acid sequence: ASTKGPSVFPLAPSSKSTSGGTAAL-GCLVKDYFPEPVTVSWNSGALTSGVHTFPAVLQSSG LYSLSSWTVPSSSLGTQTYICNVNHKPSNTKVDKRV (SEQ ID NO: 2)

In certain embodiments, the CH1 domain is a variant of SEQ ID NO: 2 and comprises 1-10, 1-5, 1-2 or 1 amino acid substitutions or deletions relative to SEQ ID NO: 2.

In an embodiment, the present disclosure provides a Fab comprising a modified heavy chain constant region, wherein the CH1 domain comprises the amino acid sequence of any one of ASTKGPSVFPLAPSSKSTSGGTAAL-GCLVKDYFPEPVTVSWNSGALTSGVHTFPAVLQSSG LYSLSSWTVPSSSLGTQTYICNVNHKPSNTKVDKKV (SEQ ID NO: 1), ASTKGPSVFPLAPSSKSTSGGTAAL-GCLVKDYFPEPVTVSWNSGALTSGVHTFPAVLQSSG LYSLSSWTVPSSSLGTQTYICNVNHKPSNTKVDKRV (SEQ ID NO: 2), ASTKGPSVFPLAPSSKSTSGGTAAL-GCLVKDYFPEPVTVSWNSGALTSGVHTFPAVLQSSG LYSLSSWTVPSSSLGTQTYICNVNHKPSNTKVDKKI (SEQ ID NO: 7), ASTKGPSVFPLAPSSKSTSGGTAAL-GCLVKDYFPEPVTVSWNSGALTSGVHTFPAVLQSSG LYSLSSWTVPSSSLGTQTYICNVNHKPSNTKVEKKV (SEQ ID NO: 8), ASTKGPSVFPLAPSSKSTSGGTAAL-GCLVKDYFPEPVTVSWNSGALTSGVHTFPAVLQSSG LYSLSSWTVPSSSLGTQTYICNVNHKPSNTKVDKGV (SEQ ID NO: 9), ASTKGPSVFPLAPSSKSTSGGTAAL-GCLVKDYFPEPVTVSWNSGALTSGVHTFPAVLQSSG LYSLSSWTVPSSSLGTQTYICNVNHKPSNTKVDKEV (SEQ ID NO: 10) ASTKGPSVFPLAPSSKSTSGGTAAL-GCLVKDYFPEPVTVSWNSGALTSGVHTFPAVLQSSG (SEQ ID NO: 104), or an amino acid sequence that differs from SEQ ID NO 1, 2, 7, 8, 9, or 10 in at most 5 amino acids or is at least 95% identical to SEQ ID NO 1, 2, 7, 8, 9, or 10.

In certain embodiments, the present disclosure provides a Fab comprising a modified heavy chain constant region, wherein the heavy chain constant region comprises a CH1 domain comprising the sequence ASTKGPSVF-PLAPSSKSTSGGTAALGCLVKDYF-PEPVTVSWNSGALTSGVHTFPAVLQSSG LYSLSS-WTVPSSSLGTQTYICNVNHKPSNTKVDKRV (SEQ ID NO: 2) or an amino acid sequence that differs from SEQ ID NO: 2 in at most 10 amino acids or is at least 90% identical to SEQ ID NO: 2, wherein at least one of D212, R214, V215 is substituted with any amino acid residue except cysteine.

Hinge Region

In an embodiment, the modified heavy chain constant region may comprise an amino acid sequence comprising one or more amino acid residues of a wildtype rat IgG1 hinge (SEQ ID NO: 16), rat IgG2a hinge (SEQ ID NO: 22), rat IgG2b hinge (SEQ ID NO: 27), rat IgG2c hinge (SEQ ID NO: 35) or mouse IgG1 hinge (SEQ ID NO: 37), mouse IgG2a hinge (SEQ ID NO: 43), mouse IgG2b hinge (SEQ ID NO: 48), mouse IgG2c hinge (SEQ ID NO: 54), mouse IgG3 hinge (SEQ ID NO: 50), or an amino acid sequence that is at least 80%, 85%, 90%, 95% identical to the corresponding amino acid sequence of a wildtype rat or mouse IgG hinge region.

Also provided are Fabs comprising a modified heavy chain constant region, wherein the modified heavy chain constant region comprises a wildtype rat or mouse hinge region, wherein the hinge comprises up to 1, 2, 3, 4, 5, 6, 7, 8, 9, 10, 11, 12, 13, 14, 15, 16, 17, 18, 19, 20, 21, 1-2, 1-3, 1-5, 3-5, 1-10, 3-10, 5-10, 1-21, 5-21, 10-21 and/or at most 21, 15, 12, 10, 9, 8, 7, 6, 5, 4, 3, 2, or 1 substitutions, deletions or additions.

In an embodiment, the modified heavy chain constant region comprises an amino acid sequence comprising one or more amino acid residues of a wildtype rat IgG1, IgG2a, IgG2b, IgG2c hinge region, or an amino acid sequence that is at least 80%, 85%, 90% or 95% identical to the corresponding amino acid sequence of a wildtype rat IgG hinge region.

In an embodiment, the rat IgG hinge region comprises a wildtype rat IgG2b hinge (SEQ ID NO: 27) and variants having 1, 2, 3, 4, 5, 6, 7, 8, 9, 10, 11, 12, 13, 14, 15, 16, 17, 18, 19, 20, 21, 1-2, 1-3, 1-5, 3-5, 1-10, 3-10, 5-10, 1-21, 5-21, 10-21 and/or at most 21, 15, 12, 10, 9, 8, 7, 6, 5, 4, 3, 2, or 1 substitutions, deletions or additions.

In an embodiment, the present disclosure provides a Fab comprising a modified heavy chain constant region, wherein the rodent hinge region is of wildtype rat IgG2a (SEQ ID NO: 22) or rat IgG2b isotype (SEQ ID NO: 27), or comprises an amino acid sequence that is at least 80%, 85%, 90% or 95% identical to the amino acid sequence of a wildtype rat IgG2a or rat IgG2b hinge region.

In an embodiment, the modified heavy chain constant region comprises an amino acid sequence comprising one or more amino acid residues of a wildtype rat IgG1 hinge region (SEQ ID NO: 16), or an amino acid sequence that is at least 80%, 85%, 90% or 95% identical to the corresponding amino acid sequence of a wildtype rat IgG1 hinge region.

In an embodiment, the modified heavy chain constant region comprises an amino acid sequence comprising one or more amino acid residues of a wildtype rat IgG2a hinge region (SEQ ID NO: 22), or an amino acid sequence that is at least 80%, 85%, 90% or 95% identical to the amino acid sequence of the corresponding wildtype rat IgG2a hinge region.

In an embodiment, the modified heavy chain constant region comprises an amino acid sequence comprising one or more amino acid residues of a wildtype rat IgG2b hinge region SEQ ID NO: 27), or an amino acid sequence that is at least 80%, 85%, 90% or 95% identical to the amino acid sequence of the corresponding wildtype rat IgG2b hinge region.

In an embodiment, the modified heavy chain constant region comprises an amino acid sequence comprising one or more amino acid residues of a wildtype rat IgG2c hinge region (SEQ ID NO: 35), or an amino acid sequence that is at least 80%, 85%, 90% or 95% identical to the corresponding amino acid sequence of a wildtype rat IgG2c hinge region.

In an embodiment, the present disclosure provides a Fab comprising a modified heavy chain constant region, wherein the hinge region comprises the amino acid sequence of any one of SEQ ID NO: 16-21, 22-26, 27-34, 93, 35-36, 37-42, 43-47, 48-53, 54-58, 59-60, wherein X, X2, X3 are any amino acid residue except cysteine with the proviso that X2 and X3 constitute a sequence motif which is not DG, NG or NS.

In an embodiment, the present disclosure provides a Fab comprising a modified heavy chain constant region, wherein the one more amino acid residues of the rodent hinge region are of rat IgG2b isotype and comprises the amino acid sequence of any one of SEQ ID NO: 32-34, 93, wherein X2, X3 are any amino acid residues except cysteine with the proviso that X2 and X3 constitute a sequence motif which is not DG, NG or NS.

In an embodiment, the present disclosure provides a Fab comprising a modified heavy chain constant region, wherein the hinge region comprises the amino acid sequence ERRX2X3GIGHKC (SEQ ID NO: 33), wherein X2, X3 are any amino acid residue except cysteine with the proviso that X2 and X3 constitute a sequence motif which is not DG, NG, NS.

In an embodiment, the present disclosure provides a Fab comprising a modified heavy chain constant region, wherein the hinge region comprises the amino acid sequence of any one of ERRNGGIGHKC (SEQ ID NO: 32), EERNGGIGHKC (SEQ ID NO: 93), ERRQGGIGHKC (SEQ ID NO: 34), VPREC (SEQ ID NO: 26).

If the rat or mouse hinge region comprises more than one cysteine residue, the hinge region can further contain additional modifications, for example, to reduce disulfide bond formation in order to prevent formation of $(Fab)_2$ molecules.

Exemplary rat IgG2b hinge variants according to the present disclosure include hinges in which 3 of the 4 present cysteines (C11, C14, C17, C20 in SEQ ID NO: 28-31 as shown in Table 1) are changed to another amino acid and wherein only 1 cysteine is maintained to allow disulfide bond formation between the modified heavy chain constant region and the light chain constant region of the Fab. Other such variants for rat or mouse hinges may comprise the amino acid sequence of any one of SEQ ID NO: 17-20, 23-25, 28-31, 38-41, 44-46, 49-52, 55-57. Preferably, a cysteine may be replaced by a serine.

Other exemplary rat IgG2b hinge variants of the present disclosure includes hinges in which the sequence motif “NG” present at rat IgG2b hinge position 4-5 according Table 1 is substituted with any other sequence motif with does not constitutes a potential posttranslational modification sites. Such motifs may include amongst others, “DG”, “NG”, “NS” motifs. Preferably, the substitution consists of a “QG” motif at said position.

In an embodiment, the present disclosure provides a Fab comprising a modified heavy chain constant region comprising a hinge region comprising the sequence ERRQGGIGHKC (SEQ ID NO: 34) or an amino acid sequence that differs from SEQ ID NO: 34 in at most 5 amino acids.

In an embodiment, the present disclosure provides a Fab comprising a modified heavy chain constant region comprising a hinge region comprising the sequence ERRQGGIGHKC (SEQ ID NO: 34).

CH1+Hinge

A Fab comprising a modified heavy chain constant region may comprise a human IgG1 CH1 domain or variant thereof and one or more amino acid residues of a rodent IgG hinge or any variant thereof. More specifically, a Fab comprising a modified heavy chain constant region may comprise a human IgG1 CH1 domain or variant thereof and one or more amino acid residues of a rat IgG2a or rat IgG2b hinge or variants thereof.

The hinge and CH1 domain may be any combination of any rat IgG2a or rat lgG2b hinge region and CH1 domain described herein.

In an embodiment, the present disclosure provides a Fab comprising a modified heavy chain constant region, comprising a CH1 domain and one or more amino acid residues of a hinge region in order from N- to C-terminus, and wherein (a) the CH1 domain comprises an amino acid sequence of any one of SEQ ID NO: 1, SEQ ID NO: 2, SEQ ID NO: 7-10, or an amino acid sequence that differs therefrom in at most 5 amino acids or which is at least 95% identical to SEQ ID NO: 1, SEQ ID NO: 2, SEQ ID NO: 7-10, and (b) a hinge region comprising any amino acid sequence of any one of SEQ ID NO: 17-21, 23-26, 28-36, 93, 38-42, 44-47, 49-53, 55-58, 59-60 or a sequence which differs therefrom in at most 5 amino acids, wherein X, X2, X3 are any amino acid residues except cysteine with the proviso that X2 and X3 constitute a sequence motif which is not DG, NG or NS.

In an embodiment, the present disclosure provides a Fab comprising a modified heavy chain constant region, comprising a CH1 domain and a hinge region in order from N- to C-terminus, and wherein (a) the CH1 domain consists of the amino acid sequence ASTKGPSVFPLAPSSKST-SGGTAALGCLVKDYFREPVTVSWNSGALT-SGVHTFPAVLQSSG LYSLSS-WTVPSSSLGTQTYICNVNHKPSNTKVDKEV (SEQ ID NO: 10) and (b) the hinge region consists of the amino acid sequence ERRQGGIGHKC (SEQ ID NO: 34).

In an embodiment, the present disclosure provides a Fab comprising a modified heavy chain constant region comprising an amino acid sequence selected from the group consisting of SEQ ID NO: 70-76.

In certain embodiments, a Fab according to the present disclosure comprises a modified heavy chain constant region, wherein the heavy chain constant region comprises the sequence of any one of:

ASTKGPSVFPLAPSSKSTSGGTAALGCLVKDYF-PEPVTVSWNSGALTSGVHTFPAVLQSSG LYS-LSSVVTVPSSSLGTQTYICNVNHKPSNTKVDK-KIVPREC (SEQ ID NO: 70) or an amino acid sequence that differs from SEQ ID NO: 70 in at most 10 amino acids or is at least 90% identical to SEQ ID NO: 70;

ASTKGPSVFPLAPSSKSTSGGTAALGCLVKDYF-PEPVTVSWNSGALTSGVHTFPAVLQSSG LYSLSS-WTVPSSSLGTQTYICNVNHKPSNTKVDKKVERRNG-GIGHKC (SEQ ID NO: 71) or an amino acid sequence that differs from SEQ ID NO: 71 in at most 10 amino acids or is at least 90% identical to SEQ ID NO: 71;

ASTKGPSVFPLAPSSKSTSGGTAALGCLVKDYF-PEPVTVSWNSGALTSGVHTFPAVLQSSG LYSLSSV-VIVPSSSLGTQTYICNVNHKPSNTKVEKKVERRNG-GIGHKC (SEQ ID NO: 72) or an amino acid sequence that differs from SEQ ID NO: 72 in at most 10 amino acids or is at least 90% identical to SEQ ID NO: 72;

ASTKGPSVFPLAPSSKSTSGGTAALGCLVKDYF-PEPVTVSWNSGALTSGVHTFPAVLQSSG LYSLSS-WTVPSSSLGTQTYICNVNHKPSNTKVDKGVERRNG-GIGHKC (SEQ ID NO: 73), or an amino acid sequence that differs from SEQ ID NO: 73 in at most 10 amino acids or is at least 90% identical to SEQ ID NO: 73;

ASTKGPSVFPLAPSSKSTSGGTAALGCLVKDYF-PEPVTVSWNSGALTSGVHTFPAVLQSSG LYSLSS-WTVPSSSLGTQTYICNVNHKPSNTKVDKEVERRNG-GIGHKC (SEQ ID NO: 74), or an amino acid sequence that differs from SEQ ID NO: 74 in at most 10 amino acids or is at least 90% identical to SEQ ID NO: 74;

ASTKGPSVFPLAPSSKSTSGGTAALGCLVKDYF-PEPVTVSWNSGALTSGVHTFPAVLQSSG LYS-LSSVVTVPSSSLGTQTYICNVNHKPSNTKVDKKVEE RNGGIGHKC (SEQ ID NO: 75), or an amino acid sequence that differs from SEQ ID NO: 75 in at most 10 amino acids or is at least 90% identical to SEQ ID NO: 75;

ASTKGPSVFPLAPSSKSTSGGTAALGCLVKDYF-PEPVTVSWNSGALTSGVHTFPAVLQSSG LYSLSS-WTVPSSSLGTQTYICNVNHKPSNTKVDKEVERRQG-GIGHKC (SEQ ID NO: 76), or an amino acid sequence that differs from SEQ ID NO: 76 in at most 10 amino acids or is at least 90% identical to SEQ ID NO: 76.

Methods for Preparing Fab Molecules Bearing a Modified Heavy Chain Constant Domain Methods for preparing a Fab comprising a modified heavy chain constant region are provided.

In an aspect of the present disclosure, an amino acid sequence comprising one or more amino acid residues at the C-terminal end of the heavy chain of a Fab are substituted by a different amino acid sequence. In principle, any substitution may be appropriate which preserves the specific binding of the Fab to its target antigen but which prevents the recognition of the Fab from binding of pre-existing anti-Fab antibodies present in a host's serum.

Accordingly, the Fab comprising an unmodified heavy chain constant region (e.g., being fully human) includes a sequence which forms an epitope that is recognized by pre-existing anti-Fab antibodies. The amino acid sequence of the epitope that is involved in the binding of pre-existing anti-Fab antibodies is referred to as the "auto-antigenic sequence".

In order to determine whether an amino acid sequence acts as an auto-antigenic sequence, peptide constructs comprising the specific sequence to be tested can be exposed to human sera to determine whether antibodies are present in the sera which recognize and specifically bind to the peptide constructs. More specifically, in order to identify whether a particular amino acid sequence of an immunoglobulin is an auto-antigenic sequence, IgG molecules can, for example, be cleaved with a panel of proteases to provide IgG fragments that contain different hinge region sequences at the C-terminal end. Alternatively, peptides and polypeptides can be produced by peptide synthesis or recombinant DNA technology which are modelled upon the sequence of the hinge region. In either case, human sera can be screened to determine whether pre-existing antibodies are present which bind to a particular exposed C-terminal sequence or synthetic peptide, respectively.

A human IgG1 hinge region derived human pre-immunity sequence having the sequence CDKTH (SEQ ID NO: 77) was identified from observations made concerning the nature of pre-existing human immunity and induced immune responses to a murine Fab and its chimeric (rat/human) Fab counterpart (see WO94/11028). Other potential auto-antigenic sequences present in the human IgG1 hinge region may include PKSCD (SEQ ID NO: 61), EPKSC (SEQ ID NO: 94), KSCDK (SEQ ID NO: 62), SCDKT (SEQ ID NO: 63), DKTHT (SEQ ID NO: 64), KTHTC (SEQ ID NO: 65), THTCP (SEQ ID NO: 66), HTCPP (SEQ ID NO: 67), TCPPC (SEQ ID NO: 68) and CPPCP (SEQ ID NO: 69). These peptides cover the entire human IgG1 hinge region.

Accordingly, removing the entire human hinge region of a fully human Fab or any parts thereof may prevent the binding of pre-existing anti-Fab antibodies present in human serum.

The inventors of the present disclosure determined that the substitution of a rat for a human hinge region in a Fab comprising a human CH1 domain prevented the binding of anti-Fab antibodies present in human plasma samples and also prevented unwanted target receptor activation caused by anti-Fab antibodies present in said plasma samples.

In a preferred embodiment, the non-auto-antigenic sequence is derived from a rodent IgG heavy chain constant region. More specifically, the non-auto-antigenic sequence is derived from the rodent hinge region. More specifically, the non-auto-antigenic sequence is derived from a rat hinge region. More specifically, the non-auto-antigenic sequence comprises one or more amino acid residues of the rat hinge region is of the rat IgG2a or IgG2b isotype.

In an embodiment, the present disclosure provides a method of preparing a Fab comprising a modified heavy chain constant region, wherein the Fab comprises a CH1 domain and a hinge region in order from N- to C-terminus, comprising the steps of:

(a) providing a Fab comprising a hinge that is not a rodent IgG hinge region;

(b) replacing the non-rodent hinge with one or more amino acid residues of a rodent hinge region, respectively.

The Fab of the present disclosure may be derived from any animal, such as from human, mouse, rat, rabbit, goat or camel. In an aspect of the present disclosure, the Fab is a human or humanized Fab. In an embodiment, the non-rodent IgG hinge region is of human IgG1, IgG2, IgG3 or IgG4 isotype and comprises an amino acid sequence as set forth in SEQ ID NO: 11-15. In an embodiment, the non-rodent IgG hinge region comprises a human IgG1 hinge region comprising the sequence EPKSC (SEQ ID NO: 94).

In an embodiment, the non-rodent hinge region is of human IgG1 isotype and may comprises 1, 2, 3, 4, 5, 6, 7, 8, 9, or 10 substitution or deletions of the amino acid sequence EPKSCDKTHTCPPCP (SEQ ID NO: 11).

In an embodiment, the non-rodent hinge region comprises the amino acid sequence selected from the group consisting of EPKSCDKT SEQ ID NO 78, EPKSCDKTHT SEQ ID NO: 79, EPKSCDKTH SEQ ID NO: 80, EPKSCDK SEQ ID NO: 81, EPKSCD SEQ ID NO: 82, EPKSC (SEQ ID NO: 94), EPKS SEQ ID NO: 83, EPK SEQ ID NO: 84, EP SEQ ID NO: 85, PKSCD (SEQ ID NO: 61), KSCDK (SEQ ID NO: 62), SCDKT (SEQ ID NO: 63), DKTHT (SEQ ID NO: 64), KTHTC (SEQ ID NO: 65), THTCP (SEQ ID NO: 66), HTCPP (SEQ ID NO: 67), TCPPC (SEQ ID NO: 68) and CPPCP (SEQ ID NO: 69).

The isotype of the rodent hinge may be of the same isotype (e.g. human IgG1 vs. mouse IgG1) or different isotype (e.g. human IgG1 vs. mouse IgG2a) as the non-rodent hinge region.

In an embodiment of the disclosure, the method comprises the step of replacing one or more amino acid residues of the non-rodent hinge comprising the amino acid sequence EPKSC (SEQ ID NO: 94) with a rodent hinge region comprising any one of SEQ ID NO: 17-21, 23-26, 28-34, 93, 35-36, 38-42, 44-47, 49-53, 55-58, or 59-60 or a sequence which differs therefrom in at most 5 amino acids, wherein X, X2, X3 are any amino acid residue except cysteine with the proviso that X2 and X3 constitute a sequence motif which is not DG, NG or NS.

In an aspect of the present disclosure, the rodent hinge region comprises only one cysteine which allows the formation of a disulfide bond between the heavy chain and the light chain of the Fab and thus stabilizes the molecule. Said cysteine may be located at the C-terminus of the hinge region. In a particular embodiment, said cysteine is the last amino-acid residue of the modified heavy chain constant region of the Fab of the present disclosure. In further aspects of the present disclosure, the cysteine does not allow the formation of disulfide bonds between the heavy chain constant region of a first Fab molecule and the heavy chain constant region of a second Fab molecule. In a further aspect of the present disclosure, the rodent hinge region prevents the formation of $(Fab)_2$ molecules. In a further aspect of the present disclosure, the rodent hinge region of the Fab molecule of the present disclosure contains not more than one cysteine.

In an embodiment of the disclosure, the method comprises the step of replacing the non-rodent hinge amino acid sequence EPKSC (SEQ ID NO: 94) with the truncated rat IgG2a hinge region sequence VPREC (SEQ ID NO: 26)

In an embodiment of the disclosure, the method comprises the step of replacing the non-rodent hinge amino acid sequence EPKSC (SEQ ID NO: 94) with the truncated rat IgG2a hinge region sequence VPREC (SEQ ID NO: 26) or a sequence which differs therefrom in at most 1, 2, 3, 4, or 5 amino acid(s).

In an embodiment of the disclosure, the method comprises the step of replacing the non-rodent hinge amino acid sequence EPKSC (SEQ ID NO: 94) with the truncated rat IgG2b hinge region sequence ERRQGGIGHKC (SEQ ID NO: 34).

In an embodiment of the disclosure, the method comprises the step of replacing the non-rodent hinge amino acid sequence EPKSC (SEQ ID NO: 94) with a truncated rat IgG2b hinge region sequence ERRQGGIGHKC (SEQ ID NO: 34), ERRNGGIGHKC (SEQ ID NO: 32) or EERNGGIGHKC (SEQ ID NO: 93).

In an embodiment of the disclosure, the method comprises the step of replacing the non-rodent hinge amino acid sequence EPKSC (SEQ ID NO: 94) with the truncated rat IgG2b hinge region sequence ERRQGGIGHKC (SEQ ID NO: 34) or a sequence which differs therefrom in at most 1, 2, 4, or 5 amino acid(s).

It is within the scope of the disclosure, that the rodent hinge sequences may comprise additional amino-acid substitution, for instance in order to remove potential post-translational modification sites or potential T-cell epitopes present in a produced Fab of the present disclosure.

The rodent hinge region sequences comprising a non-auto-antigenic sequence disclosed herein can be incorporated into a heavy chain constant region of a Fab by a variety of means that can be readily practiced by those having ordinary skill in the art. According to the invention, such a molecule can be produced by standard recombinant DNA techniques used to produce antibodies. For example, a nucleotide sequence encoding the non-auto-antigenic hinge region sequence can be inserted at the 3' end of a gene encoding the CH1 domain of the Fab molecule. The nucleotide sequence is inserted in the proper reading frame such that the residues encoded by it will occur at the very end of the resulting protein. Regardless of the method of fusing the rodent hinge sequence to the Fab CH1 domain, the Fab is converted to a Fab comprising a modified heavy chain constant region, wherein the inserted hinge sequence does not serve as an epitope for pre-existing antibodies present in human serum. Techniques for engineering antibodies are well known and described in Winter and Millstein (1991) Nature 349:293, and Larrich and Fry (1991) Hum. Antibod. and Hybridomas 2:17, both of which are incorporated herein by reference.

In certain embodiments, the present disclosure provides a nucleic acid encoding the Fab comprising a modified heavy chain constant region of the present disclosure.

In certain embodiments, the present disclosure provides a vector comprising the nucleic acid molecules encoding the Fab comprising a modified heavy chain constant region of the present disclosure. In certain embodiments, the vector is an expression vector.

In certain embodiments, the present disclosure provides a recombinant host cell comprising the nucleic acid molecule or the vector encoding the Fab comprising a modified heavy chain constant region of the present disclosure.

In certain aspects of the present disclosure, additional amino acid residues at the C-terminal end of the modified heavy chain constant region are added for example to aid in the expression or purification or to increase the stability of the Fab of the present disclosure.

The coding sequences for the heavy and light chain of the Fab of the present disclosure can be recombinant DNA molecules, which are introduced into expression vectors by operatively linking the DNA to the necessary expression control regions (e.g. regulatory regions) required for gene expression The skilled man will realize that the polynucleotides encoding the heavy or light chain can be cloned into different vectors or in the same vector. In a preferred embodiment, said polynucleotides are cloned in the same vector. The vectors can be introduced into the appropriate host cells such as prokaryotic (e.g., bacterial) or eukaryotic (e.g., yeast or mammalian) cells by methods well known in the art (see e.g., "Current Protocol in Molecular Biology", Ausubel et al. (eds.), Greene Publishing Assoc. and John Wiley Interscience, New York, 1989 and 1992). Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence.

Upon expression in host cells, the Fabs of the present disclosure is obtained. These steps can be achieved in different ways, as will be known by the person skilled in the art. In general, such steps typically include transforming or transfecting a suitable host cell with a nucleic acid or vector or an infectious particle which encodes the Fab molecule. Further, such steps typically include culturing said host cells under conditions suitable for the proliferation (multiplication, growth) of said host cells and a culturing step under conditions suitable for the production (expression, synthesis) of the encoded Fabs. The culturing of host cells under conditions suitable for proliferation or expression is typically accomplished in the presence of media comprising components suitable for cell growth or induction of expression. In particular embodiments, the methods for the production of Fab molecules of the present disclosure further comprise the step of isolating the produced Fab from the host cells or medium.

Depending on the expression system and host selected, the Fabs of the present disclosure are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

The Fabs of the present disclosure can then be purified by a number of techniques as known to the person skilled in the art. It should be noted that Fabs of the disclosure are not naturally occurring proteins. Typically, the Fabs of the present disclosure are recombinant, synthetic or semi-synthetic amino acid sequences, polypeptides or proteins.

Functionality

In general, the Fabs of the present disclosure can be used to prevent or to inhibit the interaction between one or more target molecules of interest and their corresponding receptors or natural binding partners, thereby preventing, inhibiting or reducing the signaling pathways that are mediated by those target molecules of interest and/or modulating the biological pathways and mechanisms in which those target molecules of interest are involved.

Methods for assaying for functional activity may utilize binding assays, such as the enzyme-linked immunosorbent assay (ELISA), radioimmunoassay (RIA), fluorescence activated cell sorting (FACS) and other methods that are well known in the art (see Hampton, R. et al. (1990; Serological Methods a Laboratory Manual, APS Press, St Paul, Minn.) and Maddox, D. E. et al. (1983; J. Exp. Med. 158:1211-1216). Alternatively, assays may test the ability of the Fab of the present disclosure in eliciting a biological response as a result of binding to a biological target, either in vivo or in vitro. Such assays include B cell and T cell proliferation assays, and inhibition of proliferation assays (see Paul et al., (1991). Other suitable assays will be known to those of skill in the art.

The Fabs according to the present disclosure (i.e., Fabs having a modified heavy chain constant region) may exhibit one or more enhanced or altered features, compared to the same Fab without a modified heavy chain constant region. These features may include prevention of recognition of the Fab by pre-existing anti-Fab antibodies present in serum, in particular human serum, reduced formation of large cross-linked complexes, reduced receptor mediated signaling caused by the presence of pre-existing anti-Fab antibodies or an antagonist activity.

The prevention of binding of anti-Fab antibodies present in serum can be assessed by a serum ELISA or by any in vitro assays suited to assess target activation.

Herein, the "prevention of recognition by" or "prevention of recognition binding of" anti-Fab antibodies" means that after replacing the non-rodent hinge of a Fab with one or more amino acid residues of a rodent IgG hinge region, the anti-Fab antibodies display less than 95%, less than 90%, less than 80%, less than 50%, less than 10%, less than 5%, less than 1% binding to the Fab comprising a modified heavy chain constant region. The binding activity can be determined by methods known to those skilled in the art, for example by ELISA or by using Biacore.

Alternatively, the "prevention of recognition by" or "prevention of recognition binding of" anti-Fab antibodies" means that the Fab molecules of the present disclosure do not from aggregates due to the presence of anti-Fab antibodies present in serum. Aggregate formation can be determined by methods known to those skilled in the art, for example by using size exclusion chromatography or dynamic light scattering.

Alternatively, the "prevention of recognition by" or "prevention of binding of" means that the Fab molecules of the present disclosure do not cross-link and activate their target antigen due to the presence of anti-Fab antibodies present in serum. If the target antigen is for instance a cell surface receptor, such cross-linking may mimic the activity of natural ligands of the receptor resulting in receptor activation. In other words, a Fab may act as agonist instead of acting as antagonists. An antagonist which neutralizes the antigen's function or an agonistic molecule that activates the function of an antigen can be assessed by assaying an in vivo marker that reflects the function of the antigen.

In certain embodiments, a Fab comprising a modified heavy chain constant region according to the present disclosure has the ability to reduce formation of larger Fab/antigen cross-linked complexes, relative to a same Fab that does not comprise a modified heavy chain constant region, wherein the antibody comprises a modified heavy chain constant region selected from the group consisting of SEQ ID NOs: 70-76. Fab/antigen complexes formed with a Fab that comprises a modified heavy chain constant region may be at least 2 fold, 3 fold, 5 fold or 10 folder smaller than complexes formed with the same Fab that does not comprise a modified heavy chain constant region.

In certain embodiments, a Fab comprising a modified heavy chain constant region has a more potent antagonist or blocking activity, relative to the same Fab that does not comprise a modified heavy chain constant region, wherein the antibody comprises a modified heavy chain constant region selected from the group consisting of SEQ ID NOs: 70-76. The enhanced antagonist activity of an antagonist which neutralizes the antigen's function can be assessed by assaying an in vivo marker that reflects the function of the antigen. The antagonist activity may be enhanced by at least 10%, 30%, 50%, 75%, 2 fold, 3 fold, 5 fold or more.

In certain embodiments, a Fab comprising a modified heavy chain constant region transduces a different type of signaling or signal transduction, relative to the same antibody that does not comprise a modified heavy chain constant region, wherein the antibody comprises a modified heavy chain constant region selected from the group consisting of SEQ ID NOs: 70-76. Signal transduction can be monitored by determining the level of activation of one or more proteins in signal transduction pathways. Signal transduction triggered by a Fab that comprises a modified heavy chain constant region may be higher or lower by at least 2 fold, 5 fold or more than signal transduction with the same antibody that does not comprise a modified heavy chain constant region.

Certain methods provided herein include methods of preventing recognition of a Fab by anti-Fab antibodies present in a host's serum, reduced formation of large cross-linked complexes, reduced receptor mediated signaling caused by presence of pre-existing antibodies or antagonist activity as compared to the same Fab comprising a hinge of a non-rat or mouse IgG isotype.

Such methods comprise the steps of providing a Fab having a hinge that is not an rodent IgG hinge region, and replacing the hinge region with one or more amino acid residues of a rodent IgG hinge (such as a hinge or any parts thereof that is a wildtype rat IgG2a or IgG2b hinge, a hinge having an amino acid sequence that is at least 80%, 85%, 90%, 95% identical to the amino acid sequence of a wildtype rat IgG2a or rat IgG2b hinge region).

Accordingly, the present disclosure provides a method of preventing the recognition of a Fab by anti-Fab antibodies present in serum, comprising:

(a) providing a Fab comprising a hinge region that is not a rodent IgG hinge region;
(b) replacing the hinge region with one or more amino acid residues of a rodent IgG hinge region, respectively.

Accordingly, the present disclosure provides a method of preventing of receptor activation by anti-Fab antibodies present in serum when an anti-receptor Fab is used, comprising:

(a) providing a Fab comprising a hinge region that is not a rodent IgG hinge region;
(b) replacing the hinge with one or more amino acid residues of a rodent IgG hinge region, respectively.

A rodent IgG hinge may be a wildtype rat IgG2a or rat IgG2b hinge, or comprises an amino acid sequence that is at least 80%, 95% 90%, 95% identical to the amino acid sequence of a wildtype rat IgG2a or rat IgG2b hinge and may comprise, e.g., any sequence set forth in Table 1.

In an embodiment of the disclosure, the method comprises the step of replacing one or more amino acid residues of the non-rodent hinge comprising the amino acid sequence EPKSC (SEQ ID NO: 94) with a rodent hinge region comprising any one of SEQ ID NOs: SEQ ID NO: 17-21, 23-26, 28-34, 93, 35-36, 38-42, 44-47, 49-53, 55-58, or 59-60 or a sequence which differs therefrom in at most 5 amino acids, wherein X, X2, X3 are any amino acid residues except cysteine with the proviso that X2 and X3 constitute a sequence motif which is not DG, NG or NS.

In another aspect of the present disclosure, the Fab of the present disclosure prevents cross-linking of a target antigen due to the presence of anti-Fab antibodies present in serum, wherein the Fab comprises a modified heavy chain constant region selected from the group of SEQ ID NOs: 70-76.

In another aspect of the present disclosure, the presence of the modified heavy chain constant region prevents cross-linking of one or more Fab molecules of the present disclosure due to the presence of anti-Fab antibodies present in serum, wherein the modified heavy chain constant region is selected from the group consisting of SEQ ID NOs: 70-76.

In a further aspect of the present disclosure, the Fab of the present disclosure does not from aggregates due to the presence of anti-Fab antibodies present in serum, wherein the Fab comprises a modified heavy chain constant region selected from the group of SEQ ID NO: 70-76.

In certain embodiments, a Fab comprising a modified heavy chain constant region binds specifically to a cell surface molecule and triggers intracellular signaling, wherein the Fab comprises a modified heavy chain constant region selected from the group of SEQ ID NO: 70-76. In certain aspect of the disclosure, intracellular signaling mediates antagonist activity. In certain embodiments, the Fab inhibits more potent intracellular signaling relative to a Fab having the same variable regions and light chain, but comprising a wild-type human IgG1 heavy chain constant region.

In certain embodiments, a Fab comprising a modified heavy chain constant region binds specifically to a cell surface molecule and prevents formation of high molecular weight antibody-cell surface molecule complexes, wherein the Fab comprises a modified heavy chain constant region selected from the group of SEQ ID NO: 70-76. In certain embodiments, the antibody prevents formation of higher molecular weight complexes relative to a Fab having the same variable regions and light chain, but comprising a wildtype human IgG1 heavy chain constant region.

In certain embodiments, a Fab comprising a modified heavy chain constant region binds specifically to a cell surface molecule and prevents clustering or oligomerization of the cell surface molecule, wherein the Fab comprises a modified heavy chain constant region selected from the group of SEQ ID NO: 70-77. In certain embodiments, the Fab prevents or reduces clustering or oligomerization of the cell surface molecule relative to an Fab having the same variable regions and light chain, but comprising an wildtype human IgG1 heavy chain constant region.

Pharmaceutical Compositions

The Fab of the present disclosure comprising a modified heavy chain constant region may be used for the prevention and treatment of diseases and disorders which are mediated by biological pathway(s) in which the target molecule of interest, against which the Fab of the present disclosure is directed to, is involved.

In certain embodiments, the present disclosure provides pharmaceutical compositions comprising one or more Fab molecules of the present disclosure obtainable by the methods of the present disclosure and optionally at least one pharmaceutically acceptable carrier together referred to herein as pharmaceutical compositions. The pharmaceutical compositions may further comprise at least one other pharmaceutically active compound. The pharmaceutical compositions of the present disclosure can be used in the diagnosis, prevention and/or treatment of diseases and disorders associated with a target molecule of interest.

In particular, the present disclosure provides pharmaceutical compositions comprising a Fab comprising a modified heavy chain constant region that are suitable for prophylactic, therapeutic and/or diagnostic use in a warm-blooded animal, and in particular in a mammal, and more in particular in a human being. Generally, the Fab of the present disclosure may be formulated as a pharmaceutical preparation or compositions comprising at least one Fab according to the present disclosure and at least one pharmaceutically acceptable carrier, diluent or excipient and/or adjuvant, and optionally one or more further pharmaceutically active polypeptides and/or compounds. Such a formulation may be suitable for oral, parenteral, topical administration or for administration by inhalation.

In particular, the Fab comprising a modified heavy chain constant region according to the present disclosure may be used in combination with other pharmaceutically active compounds that are or can be used for the prevention and/or treatment of the diseases and disorders in which a target molecule of interest is involved, as a result of which a synergistic effect may or may not be obtained. Examples of such compounds, as well as routes, methods and pharmaceutical formulations or compositions for administering them will be clear to the clinician.

In an embodiment, the present disclosure provides a pharmaceutical composition comprising one or more Fabs of the present disclosure for use in the prevention and/or treatment of a disorder or condition associated with the undesired presence of a target molecule of interest specifically bound by the one or more Fab molecules.

In an embodiment, the present disclosure provides a pharmaceutical composition comprising one or more modified Fabs of the present disclosure for use in the prevention of undesired side effect caused by the presence of pre-existing or newly formed anti-Fab antibodies.

In an embodiment, the present disclosure provides a pharmaceutical composition comprising one or more modified Fabs of the present disclosure for the use as a medicament.

In an embodiment, the disclosure provides a pharmaceutical composition comprising one or more Fabs of the present disclosure for use in the prevention and/or treatment of autoimmune diseases, inflammatory diseases, cancer, neovascular diseases, infectious diseases, thrombosis, myocardial infarction, and/or diabetes.

In a further embodiment, the disclosure provides a method for the treatment of autoimmune diseases, inflammatory diseases, cancer, neovascular diseases, infectious diseases, thrombosis, myocardial infarction, and/or diabetes in a subject in need thereof using a pharmaceutical composition comprising one or more Fabs comprising a modified heavy chain constant region according to the present disclosure.

In an embodiment, the disclosure provides a pharmaceutical composition comprising one or more Fabs comprising a modified heavy chain constant region for use in the treatment of certain clinical indications, as for example thrombotic and vascular diseases, acute coronary syndrome, percutaneous coronary intervention, ischemic stroke, carotid artery stenosis or peripheral arterial occlusive disease. Furthermore it could be used for the prevention of restenosis and atherosclerosis.

WORKING EXAMPLES

Example 1: Design of the Modified Heavy Chain Constant Region

As a starting point, a fully human Fab molecule (Ref-Fab#1) against Receptor-X was selected. The Fab molecule is based on the human IgG1 isotype and its heavy chain C-terminally ends at position 220 (EU numbering). The Fab is based on a natural IgG1 allotype which bears a K214R mutation in the CH1 domain (SEQ ID NO: 2).

Receptor-X is a cell surface receptor which becomes activated after ligand interaction and subsequent Receptor-X clustering. Experimental studies demonstrated that bivalent therapeutics, like IgGs, are able to mimic ligand function and strongly activate the receptor. Like the above referenced IgGs, Ref-Fab#1 induces receptor activation in the presence of human plasma samples obtained from healthy donors (see FIG. 2B). This finding strongly indicates that the fully human Fab is bound by pre-existing anti-Fab antibodies present in the tested plasma samples. Binding of anti-Fab antibodies is suggested to cross-link Fab molecules leading to receptor clustering and subsequent receptor-activation.

Accordingly, the design of the modified non-auto-antigenic Fab heavy chain constant region of the present disclosure was supported by the findings described in WO94/11028. WO94/11028 teaches that the whole hinge region of a human IgG1 or any fragments thereof may act as auto-antigenic sequences which are recognized by anti-Fab antibodies present in human serum. The findings of WO94/11028 were confirmed by the inventors of the present disclosure by using a rat derived IgG2a molecule (Ref-IgG#2) directed to Receptor-X. Because of its bivalent structure, the IgG induces strong receptor activation, whereas a corresponding rat Fab fragment (Ref-Fab#2) prepared by papain digest, shows no signs of receptor activation in presence of human serum samples (see FIG. 2B). These finding indicate that the enzymatically generated rat hinge sequence present at the C-terminal end of the Fab heavy chain does not form an epitope which is recognized by pre-existing anti-human Fab antibodies.

In order to select the optimal sequence for the generation of a modified human heavy chain constant region which is not recognized by human anti-Fab antibodies, the inventors decided to exchange the entire hinge region sequence of the human Fab comprising SEQ ID NO: 94. The stretch was replaced with a rat IgG2a hinge sequence consisting of SEQ ID NO: 26 resulting in Fab Construct #1 or with the rat IgG2b hinge sequence consisting of SEQ ID NO: 32 resulting in Fab Construct #2. The C-terminally present cysteine residue in both constructs allowed disulfide formation between the modified heavy chain and unmodified light chain of the Fab. Additional cysteines were avoided to prevent disulfide bond formation between the heavy chains of two Fab molecules which would result in $(Fab)_2$ formation.

The thus obtained Fab molecules comprising a modified heavy chain constant region were produced in a mammalian line and tested in a FACS based receptor activation assays. In contrast to the corresponding fully human Fab molecule, both, Fab Construct#1 and Fab Construct #2 prevented receptor activation caused by the presence of anti-Fab antibodies in human plasma samples. However, Construct#2 revealed superior properties (see FIGS. 2A and 2B) and was subjected to further studies.

In order to minimize the risk for increased immunogenicity in human patients, an in silico T cell epitope screening for Construct#2 (Lonza, The Epibase™ In Silico tool) was performed which indeed revealed a potential T-cell epitope in the amino acid sequence of Construct#2. In order to remove said epitope, an Epibase™ mutation analysis was performed, wherein each amino-acid-position was virtually substituted with each of the natural occurring amino acid residue except cysteine. Suggested amino acid exchanges were further analyzed in silico regarding their potential structural influence. 4 variants affecting 2 positions in the human CH1 domain and 1 position in the rat hinge region (EU position 212, 214 and 217, see SEQ ID NO: 99-102, Figure: 1) were produced and characterized in vitro including ELISA binding, ligand binding inhibition and FACS based receptor activation.

Amongst the 4 variants, the K214E mutant revealed the most promising in vitro properties and was further engineered to remove the potential post-translational modification motif 'NG" at EU position 219-220 by introducing a N219Q mutation.

Accordingly, the finally preferred Fab construct (referred to as the 'EQ Construct') is comprised of a modified heavy chain constant region including a human wild-type IgG1 CH1 domain with a K214E mutation and a hinge region spanning position 216-226 consisting of the first 11 amino acids of the wildtype rat IgG2b hinge region including a N219Q mutation (see SEQ ID NO: 103 in Figure: 1).

The 'EQ construct' was incorporated into 3 Receptor-X targeting human Fab molecules for in vitro characterization. The Fab EQ constructs retained their binding to their target antigen (see FIG. 6 and Example 3-4), their antagonistic activity (see FIG. 7 and Example 5) and did not mediated receptor activation in the presence of a large panel of human serum samples (see FIG. 4 and Example 6).

Example 2: Generation and Production of Fab Molecules

For generation of fully human anti-Receptor X Fab molecules, the MorphoSys Ylanthia® library was used for pannings against to the recombinant receptor. The MorphoSys Ylanthia® library (Tiller et al. mAbs 5:3, 1-26; May/June (2013) and U.S. Pat. No. 8,728,981) is a commercially available phagemid library and employs the CysDisplay® technology for displaying the Fab on the phage surface (Lohning et al., WO2001/05950).

Functional human Fab fragments were converted from the bacterial to the mammalian Fab format by sub-cloning procedure. Antibody encoding vectors were enzymatically digested and the resulting vector backbones were ligated with the Ylanthia® mammalian expression cassette and further sub-cloned into the respective mammalian Fab vector.

For generation of the modified heavy chain constant regions according to the present disclosure, the DNA encoding the entire designed heavy chain constant region was synthesized as double-stranded DNA fragments by an external provider (IDT). The resulting synthetic linear DNA fragments comprising the modified heavy chain constant region with homologous overlapping sequences were subsequently seamlessly cloned into the corresponding mammalian Fab vector by replacing the parental heavy chain constant region.

Variants for the removal of a potential T cell epitope (aa exchanges within the human CH1 domain or in the rat hinge region (see SEQ ID NO: 99-102, FIG. 1) were generated by a PCR based mutagenesis strategy. Briefly, linear DNA fragments were produced by PCR with suitable oligonucleotides harboring the favored mutations and homologous overlapping sequences and subsequently cloned into the corresponding mammalian Fab vector.

Introduction of the N219Q mutation was achieved using the by a Site-Directed Mutagenesis approach. A specific primer pair was designed and PCR-based mutagenesis applied according to manufacturer's instructions.

For expression and purification eukaryotic HKB11 cells were transfected with pYMex10 eukaryotic expression vector DNA encoding both heavy and light chains of Fabs. Cell culture supernatant was harvested on day 3 post transfection and subjected to Capture select IgG-CH1 affinity chromatography (MabSelect SURE, GE Healthcare) for antibody purification. All samples were sterile filtered (0.2 μm pore size). Purity of Fab was analyzed under denaturing, reducing and non-reducing conditions using a Labchip System (Caliper GXII, Perkin Elmer) or on SDS-PAGE. Protein concentrations were determined by UV-spectrophotometry and HP-SEC was performed to analyze IgG preparations in native state.

All Fabs were produced in exploratory-scale in HKB11 cells. All Fabs showed good expression yields (>5 mg/L) and passed quality control. Individual antibodies were produced in good quantities and successfully passed quality control in SEC (>90% monomer content). SDS-Page analysis under reducing and non-reducing conditions confirmed disulfide-bridge formation between the heavy and light chain of the Fab. Produced Fabs were tested for binding and functionality.

Example 3: Characterization of Purified Receptor-X Specific Fab EQ Constructs for ELISA Binding Target-specific binding of Receptor-X specific Fabs (RefFab#5 and RefFab#6) as EQ constructs was confirmed by ELISA.

Methods:

0.05 μg/ml of recombinant Receptor-X-Fc-fusion protein was coated on Nunc MaxiSorp™ plates. Bound Fabs were detected using an alkaline phosphatase-conjugated detection antibody (Jackson Immuno Research) directed against human $F(ab')_2$ fragment.

Results:

As indicated in Figure: 6A, both Fabs displayed specific binding to the recombinant Receptor-X protein. $EC_{50}$ values were in the sub-nanomolar range.

The results confirmed that the modified heavy chain constant region of the Fab molecules did not affect binding to the target antigen.

Example 4: Characterization of Purified Receptor-X Specific Fab EQ Constructs for Cell ELISA Binding Binding of Receptor-X specific Fabs (RefFab#5 and RefFab#6) as EQ constructs to Receptor-X expressed on CHO cells was analyzed in a cell-ELISA.

Methods:

CHO cells stably transfected with Receptor-X were seeded at a density of $5\times10^3$ cells/well in growth medium to a 96 well High Bind Plate (Meso Scale Discovery) and cultivated over night at 37° C. and 5% $CO_2$. Cells were blocked with PBS supplied with 5% BSA and then incubated with varying concentrations of Fabs diluted in PBS supplied with 0.5% BSA. After washing, bound Fabs were detected using ECL-conjugated detection antibody directed against human $F(ab')_2$ fragment (Jackson Immuno Research). MSD read buffer (Meso Scale Discovery) was added to cells prior to readout via Sector Imager6000 (Meso Scale Discovery).

Results:

As depicted in FIG. 6B, the purified Fab_EQ constructs revealed specific cell binding to Receptor-X expressed on CHO cells with $EC_{50}$ values in the single digit nanomolar range.

Again, this result confirmed that the modified heavy chain constant region of the Fab molecules did not affect binding to the native target antigen.

Example 5: Characterization of Purified Receptor-X Specific Fab EQ Constructs in a Receptor-Ligand Binding Inhibition Assay The antagonistic activity of Receptor-X specific Fabs (RefFab#5 and RefFab#6) as EQ constructs was analyzed in a MSD-based receptor-X/ligand binding inhibition assay Methods:

1 μg/ml of recombinant Receptor-X-ligand was coated on a MSD-plate and blocked with PBS supplied with 0.05% TWEEN® 20 (a polysorbate-type nonionic surfactant formed by the ethoxylation of sorbitan before the addition of lauric acid) and 5% skim milk powder. Purified recombinant Fc-conjugated Receptor-X and varying concentrations of Fab were incubated in a polypropylene plate for 30 min at RT. Fab/Receptor-X mixture was added to coated ligand for 1 h at RT. Bound Receptor-X was detected using an ECL-conjugated detection antibody directed against human Fc (Jackson Immuno Research). MSD read buffer (Meso Scale Discovery) was added prior to readout via Sector Imager6000 (Meso Scale Discovery). Inhibition of the specific Receptor-X/ligand interaction by the Fab resulted in decreasing signals.

Results:

As depicted in FIG. 7, both tested Fabs displayed significant Receptor-X ligand interaction inhibition with IC50 values in the single digit nM range.

This result confirmed that the modified heavy chain constant region of the Fab molecules did not affect the antagonistic activity of the Fab molecules.

Example 6: Characterization of Purified Receptor-X Specific Fab EQ Constructs for Receptor Activation Through Anti-Fab Antibodies The activating potential of the EQ construct, the Construct#2 with the K214E mutation and the fully human CH1 and hinge region was tested on 20 different blood samples for three different Receptor-X specific Fabs (RefFab #5-#7).

Methods:

Receptor activation and subsequent downstream signaling was evaluated by assessing the cell surface expression of a corresponding activation marker protein by fluorocytometry. Cells of interest were isolated from human blood samples. Cells in autologous human plasma were incubated with varying concentrations of Fab and incubated for 30 min at RT. Subsequently, phycoerythrin-conjugated antibody directed against the surface activation marker (BD Pharmingen) was added followed by incubation for 20 min at RT protected from light. Cells were fixated with 1% formaldehyde solution for 30 min at 4° C. and analyzed using BD FACSCANTO™ II (BD Biosciences). Basal activation marker expression was determined by incubation with PBS instead of Fab. Fab-induced Receptor-X activation is represented as level of activation marker expression in the presence of Fab normalized to basal expression level in the presence of PBS.

Results:

As shown in FIG. 4, the fully human Fab induced a significant increase in the expression of the surface activation marker on cells expressing Receptor-X in the presence of human plasma (defined as >5 fold over background in 23 samples (corresponds to 42%)). In sharp contrast, the two Fabs with the modified heavy chain constant region were much less active in this test with Construct#2_EQ showing activity only on 1 serum sample and Construct#2_K214E being not active at all.

This differential activation pattern may indicate that the activating potential of the tested Fab in this assay is not determined by the variable region of the Fabs but appears to reside in the C-terminal region of the heavy because the activity is significantly reduced by the C-terminal rat hinge region. These results clearly suggest that the fully human Fabs were recognized by anti-Fab IgG pre-existing in donors' blood, which induced receptor activation.

The invention claimed is:

1. A Fab comprising a modified heavy chain constant region, wherein said modified heavy chain constant region comprises a CH1 domain and a hinge region, wherein the hinge region is of a rodent IgG isotype and consists of the amino acid sequence of any one of ERRNGGIGHKC (SEQ ID NO: 32), EERNGGIGHKC (SEQ ID NO: 93), ERRQGGIGHKC (SEQ ID NO: 34) or VPREC (SEQ ID NO: 26) and wherein the CH1 domain is a wildtype human IgG1 CH1 domain or any allotype of a wildtype human IgG1 CH1 domain.

2. The Fab of claim 1, wherein the CH1 domain comprises at least the amino acid sequence of any one of DKKV (SEQ ID NO: 86), DKRV (SEQ ID NO: 87), EKKV (SEQ ID NO: 88), DKKI (SEQ ID NO: 89), DKGV (SEQ ID NO: 90) or DKEV (SEQ ID NO: 91) from position 212 to 215 according to EU numbering.

3. The Fab of claim 1, wherein the Fab CH1 domain consists of the amino acid sequence of any one of ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV (SEQ ID NO: 1), ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRV (SEQ ID NO: 2), ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKI (SEQ ID NO: 7), ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVEKKV (SEQ ID NO: 8), ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKGV (SEQ ID NO: 9) or ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKEV (SEQ ID NO: 10.

4. The Fab of claim 1, wherein the CH1 domain comprises the amino acid substitution. D212E, K214G, K214E, R214G, R214G or V215I.

5. The Fab of claim 1, comprising a modified heavy chain constant region comprising a CH1 domain and a hinge region in order from N- to C-terminus, and wherein the CH1 domain consists of an amino acid sequence of any one of SEQ ID NO: 1, SEQ ID NO: 2, SEQ ID NO: 7-10.

6. The Fab of claim 1, comprising a modified heavy chain constant region consisting of an amino acid sequence selected from the group consisting of SEQ ID NO: 70-76.

7. The Fab of claim 1, comprising a modified heavy chain constant region comprising a CH1 domain and a hinge region in order from N- to C-terminus, and wherein the CH1 domain consists of the amino acid sequence ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKEV (SEQ ID NO: 10) and the hinge region consists of the amino acid sequence ERRQGGIGHKC (SEQ ID NO: 34).

* * * * *

SEQUENCE LISTING

```
<160> NUMBER OF SEQ ID NOS: 104

<210> SEQ ID NO 1
<211> LENGTH: 98
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

-continued

```
Tyr Ile Cys Asn Val Asn His Lys Pro Ser Asn Thr Lys Val Asp Lys
                85                  90                  95

Lys Val


<210> SEQ ID NO 2
<211> LENGTH: 98
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val


<210> SEQ ID NO 3
<211> LENGTH: 98
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val


<210> SEQ ID NO 4
<211> LENGTH: 98
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val


<210> SEQ ID NO 5
<211> LENGTH: 98
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val


<210> SEQ ID NO 6
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (95)..(95)
<223> OTHER INFORMATION: Any amino acid except Cys
<220> FEATURE:
<221> NAME/KEY: MOD_RES
<222> LOCATION: (97)..(98)
<223> OTHER INFORMATION: Any amino acid except Cys

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Xaa Lys
                85                  90                  95

Xaa Xaa
```

```
<210> SEQ ID NO 7
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ile


<210> SEQ ID NO 8
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Glu Lys
                85                  90                  95

Lys Val


<210> SEQ ID NO 9
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 9

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Gly Val
```

<210> SEQ ID NO 10
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Glu Val
```

<210> SEQ ID NO 11
<211> LENGTH: 15
<212> TYPE: PRT
<213> ORGANISM: Homo sapiens

<400> SEQUENCE: 11

```
Glu Pro Lys Ser Cys Asp Lys Thr His Thr Cys Pro Pro Cys Pro
1               5                   10                  15
```

<210> SEQ ID NO 12
<211> LENGTH: 12
<212> TYPE: PRT
<213> ORGANISM: Homo sapiens

<400> SEQUENCE: 12

```
Glu Arg Lys Cys Cys Val Glu Cys Pro Pro Cys Pro
1               5                   10
```

-continued

<210> SEQ ID NO 13
<211> LENGTH: 17
<212> TYPE: PRT
<213> ORGANISM: Homo sapiens

<400> SEQUENCE: 13

Glu Leu Lys Thr Pro Leu Gly Asp Thr Thr His Thr Cys Pro Arg Cys
1 5 10 15

Pro

<210> SEQ ID NO 14
<211> LENGTH: 15
<212> TYPE: PRT
<213> ORGANISM: Homo sapiens

<400> SEQUENCE: 14

Glu Pro Lys Ser Cys Asp Thr Pro Pro Pro Cys Pro Arg Cys Pro
1 5 10 15

<210> SEQ ID NO 15
<211> LENGTH: 12
<212> TYPE: PRT
<213> ORGANISM: Homo sapiens

<400> SEQUENCE: 15

Glu Ser Lys Tyr Gly Pro Pro Cys Pro Ser Cys Pro
1 5 10

<210> SEQ ID NO 16
<211> LENGTH: 15
<212> TYPE: PRT
<213> ORGANISM: Rattus sp.

<400> SEQUENCE: 16

Val Pro Arg Asn Cys Gly Gly Asp Cys Lys Pro Cys Ile Cys Thr
1 5 10 15

<210> SEQ ID NO 17
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (12)..(12)
<223> OTHER INFORMATION: Any amino acid except Cys

<400> SEQUENCE: 17

Val Pro Arg Asn Xaa Gly Gly Asp Xaa Lys Pro Xaa Ile Cys Thr
1 5 10 15

<210> SEQ ID NO 18
<211> LENGTH: 15
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (14)..(14)
<223> OTHER INFORMATION: Any amino acid except Cys

<400> SEQUENCE: 18

Val Pro Arg Asn Xaa Gly Gly Asp Xaa Lys Pro Cys Ile Xaa Thr
1               5                   10                  15


<210> SEQ ID NO 19
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (12)..(12)
<223> OTHER INFORMATION: Any amino acid except Cys
<220> FEATURE:
<221> NAME/KEY: MOD_RES
<222> LOCATION: (14)..(14)
<223> OTHER INFORMATION: Any amino acid except Cys

<400> SEQUENCE: 19

Val Pro Arg Asn Xaa Gly Gly Asp Cys Lys Pro Xaa Ile Xaa Thr
1               5                   10                  15


<210> SEQ ID NO 20
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: Any amino acid except Cys
<220> FEATURE:
<221> NAME/KEY: MOD_RES
<222> LOCATION: (12)..(12)
<223> OTHER INFORMATION: Any amino acid except Cys
<220> FEATURE:
<221> NAME/KEY: MOD_RES
<222> LOCATION: (14)..(14)
<223> OTHER INFORMATION: Any amino acid except Cys

<400> SEQUENCE: 20

Val Pro Arg Asn Cys Gly Gly Asp Xaa Lys Pro Xaa Ile Xaa Thr
1               5                   10                  15
```

<210> SEQ ID NO 21
<211> LENGTH: 5
<212> TYPE: PRT
<213> ORGANISM: Rattus sp.

<400> SEQUENCE: 21

Val Pro Arg Asn Cys
1 5

<210> SEQ ID NO 22
<211> LENGTH: 11
<212> TYPE: PRT
<213> ORGANISM: Rattus sp.

<400> SEQUENCE: 22

Val Pro Arg Glu Cys Asn Pro Cys Gly Cys Thr
1 5 10

<210> SEQ ID NO 23
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (8)..(8)
<223> OTHER INFORMATION: Any amino acid except Cys
<220> FEATURE:
<221> NAME/KEY: MOD_RES
<222> LOCATION: (10)..(10)
<223> OTHER INFORMATION: Any amino acid except Cys

<400> SEQUENCE: 23

Val Pro Arg Glu Cys Asn Pro Xaa Gly Xaa Thr
1 5 10

<210> SEQ ID NO 24
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (10)..(10)
<223> OTHER INFORMATION: Any amino acid except Cys

<400> SEQUENCE: 24

Val Pro Arg Glu Xaa Asn Pro Cys Gly Xaa Thr
1 5 10

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (8)..(8)
<223> OTHER INFORMATION: Any amino acid except Cys

<400> SEQUENCE: 25

Val Pro Arg Glu Xaa Asn Pro Xaa Gly Cys Thr
1 5 10

<210> SEQ ID NO 26
<211> LENGTH: 5
<212> TYPE: PRT
<213> ORGANISM: Rattus sp.

<400> SEQUENCE: 26

Val Pro Arg Glu Cys
1 5

<210> SEQ ID NO 27
<211> LENGTH: 21
<212> TYPE: PRT
<213> ORGANISM: Rattus sp.

<400> SEQUENCE: 27

Glu Arg Arg Asn Gly Gly Ile Gly His Lys Cys Pro Thr Cys Pro Thr
1 5 10 15

Cys His Lys Cys Pro
20

<210> SEQ ID NO 28
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (14)..(14)
<223> OTHER INFORMATION: Any amino acid except Cys
<220> FEATURE:
<221> NAME/KEY: MOD_RES
<222> LOCATION: (17)..(17)
<223> OTHER INFORMATION: Any amino acid except Cys
<220> FEATURE:
<221> NAME/KEY: MOD_RES
<222> LOCATION: (20)..(20)
<223> OTHER INFORMATION: Any amino acid except Cys

<400> SEQUENCE: 28

Glu Arg Arg Asn Gly Gly Ile Gly His Lys Cys Pro Thr Xaa Pro Thr
1 5 10 15

Xaa His Lys Xaa Pro
20

<210> SEQ ID NO 29
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<220> FEATURE:
<221> NAME/KEY: MOD_RES
<222> LOCATION: (11)..(11)
<223> OTHER INFORMATION: Any amino acid except Cys
<220> FEATURE:
<221> NAME/KEY: MOD_RES
<222> LOCATION: (17)..(17)
<223> OTHER INFORMATION: Any amino acid except Cys
<220> FEATURE:
<221> NAME/KEY: MOD_RES
<222> LOCATION: (20)..(20)
<223> OTHER INFORMATION: Any amino acid except Cys

<400> SEQUENCE: 29

```
Glu Arg Arg Asn Gly Gly Ile Gly His Lys Xaa Pro Thr Cys Pro Thr
1               5                   10                  15

Xaa His Lys Xaa Pro
            20
```

<210> SEQ ID NO 30
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (11)..(11)
<223> OTHER INFORMATION: Any amino acid except Cys
<220> FEATURE:
<221> NAME/KEY: MOD_RES
<222> LOCATION: (14)..(14)
<223> OTHER INFORMATION: Any amino acid except Cys
<220> FEATURE:
<221> NAME/KEY: MOD_RES
<222> LOCATION: (20)..(20)
<223> OTHER INFORMATION: Any amino acid except Cys

<400> SEQUENCE: 30

```
Glu Arg Arg Asn Gly Gly Ile Gly His Lys Xaa Pro Thr Xaa Pro Thr
1               5                   10                  15

Cys His Lys Xaa Pro
            20
```

<210> SEQ ID NO 31
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (11)..(11)
<223> OTHER INFORMATION: Any amino acid except Cys
<220> FEATURE:
<221> NAME/KEY: MOD_RES
<222> LOCATION: (14)..(14)
<223> OTHER INFORMATION: Any amino acid except Cys
<220> FEATURE:
<221> NAME/KEY: MOD_RES
<222> LOCATION: (17)..(17)
<223> OTHER INFORMATION: Any amino acid except Cys

<400> SEQUENCE: 31

Glu Arg Arg Asn Gly Gly Ile Gly His Lys Xaa Pro Thr Xaa Pro Thr
1 5 10 15

Xaa His Lys Cys Pro
20

<210> SEQ ID NO 32
<211> LENGTH: 11
<212> TYPE: PRT
<213> ORGANISM: Rattus sp.

<400> SEQUENCE: 32

Glu Arg Arg Asn Gly Gly Ile Gly His Lys Cys
1 5 10

<210> SEQ ID NO 33
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (4)..(5)
<223> OTHER INFORMATION: Any amino acid except Cys
<220> FEATURE:
<221> NAME/KEY: source
<223> OTHER INFORMATION: /note="See specification as filed for detailed description of substitutions and preferred embodiments"

<400> SEQUENCE: 33

Glu Arg Arg Xaa Xaa Gly Ile Gly His Lys Cys
1 5 10

<210> SEQ ID NO 34
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 34

Glu Arg Arg Gln Gly Gly Ile Gly His Lys Cys
1 5 10

<210> SEQ ID NO 35
<211> LENGTH: 15
<212> TYPE: PRT
<213> ORGANISM: Rattus sp.

<400> SEQUENCE: 35

Glu Pro Arg Arg Pro Lys Pro Arg Pro Pro Thr Asp Ile Cys Ser
1 5 10 15

<210> SEQ ID NO 36
<211> LENGTH: 14
<212> TYPE: PRT
<213> ORGANISM: Rattus sp.

<400> SEQUENCE: 36

Glu Pro Arg Arg Pro Lys Pro Arg Pro Pro Thr Asp Ile Cys
1 5 10

<210> SEQ ID NO 37
<211> LENGTH: 13
<212> TYPE: PRT
<213> ORGANISM: Mus sp.

<400> SEQUENCE: 37

Val Pro Arg Asp Cys Gly Cys Lys Pro Cys Ile Cys Thr
1 5 10

<210> SEQ ID NO 38
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (7)..(7)
<223> OTHER INFORMATION: Any amino acid except Cys
<220> FEATURE:
<221> NAME/KEY: MOD_RES
<222> LOCATION: (10)..(10)
<223> OTHER INFORMATION: Any amino acid except Cys

<400> SEQUENCE: 38

Val Pro Arg Asp Xaa Gly Xaa Lys Pro Xaa Ile Cys Thr
1 5 10

<210> SEQ ID NO 39
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (7)..(7)
<223> OTHER INFORMATION: Any amino acid except Cys
<220> FEATURE:
<221> NAME/KEY: MOD_RES
<222> LOCATION: (10)..(10)
<223> OTHER INFORMATION: Any amino acid except Cys
<220> FEATURE:
<221> NAME/KEY: MOD_RES
<222> LOCATION: (12)..(12)
<223> OTHER INFORMATION: Any amino acid except Cys

<400> SEQUENCE: 39

Val Pro Arg Asp Cys Gly Xaa Lys Pro Xaa Ile Xaa Thr
1 5 10

<210> SEQ ID NO 40
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (10)..(10)
<223> OTHER INFORMATION: Any amino acid except Cys
<220> FEATURE:
<221> NAME/KEY: MOD_RES
<222> LOCATION: (12)..(12)
<223> OTHER INFORMATION: Any amino acid except Cys

<400> SEQUENCE: 40

Val Pro Arg Asp Xaa Gly Cys Lys Pro Xaa Ile Xaa Thr
1 5 10

<210> SEQ ID NO 41
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (7)..(7)
<223> OTHER INFORMATION: Any amino acid except Cys
<220> FEATURE:
<221> NAME/KEY: MOD_RES
<222> LOCATION: (12)..(12)
<223> OTHER INFORMATION: Any amino acid except Cys

<400> SEQUENCE: 41

Val Pro Arg Asp Xaa Gly Xaa Lys Pro Cys Ile Xaa Thr
1 5 10

<210> SEQ ID NO 42
<211> LENGTH: 5
<212> TYPE: PRT
<213> ORGANISM: Mus sp.

<400> SEQUENCE: 42

Val Pro Arg Asp Cys
1 5

<210> SEQ ID NO 43
<211> LENGTH: 16
<212> TYPE: PRT
<213> ORGANISM: Mus sp.

<400> SEQUENCE: 43

Glu Pro Arg Gly Pro Thr Ile Lys Pro Cys Pro Pro Cys Lys Cys Pro
1 5 10 15

<210> SEQ ID NO 44
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (13)..(13)
<223> OTHER INFORMATION: Any amino acid except Cys
<220> FEATURE:
<221> NAME/KEY: MOD_RES
<222> LOCATION: (15)..(15)
<223> OTHER INFORMATION: Any amino acid except Cys

<400> SEQUENCE: 44

Glu Pro Arg Gly Pro Thr Ile Lys Pro Cys Pro Pro Xaa Lys Xaa Pro
1 5 10 15

<210> SEQ ID NO 45
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (10)..(10)
<223> OTHER INFORMATION: Any amino acid except Cys
<220> FEATURE:
<221> NAME/KEY: MOD_RES
<222> LOCATION: (15)..(15)
<223> OTHER INFORMATION: Any amino acid except Cys

<400> SEQUENCE: 45

Glu Pro Arg Gly Pro Thr Ile Lys Pro Xaa Pro Pro Cys Lys Xaa Pro
1 5 10 15

<210> SEQ ID NO 46
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (10)..(10)
<223> OTHER INFORMATION: Any amino acid except Cys
<220> FEATURE:
<221> NAME/KEY: MOD_RES
<222> LOCATION: (13)..(13)
<223> OTHER INFORMATION: Any amino acid except Cys

<400> SEQUENCE: 46

Glu Pro Arg Gly Pro Thr Ile Lys Pro Xaa Pro Pro Xaa Lys Cys Pro
1 5 10 15

<210> SEQ ID NO 47
<211> LENGTH: 10
<212> TYPE: PRT
<213> ORGANISM: Mus sp.

<400> SEQUENCE: 47

Glu Pro Arg Gly Pro Thr Ile Lys Pro Cys
1 5 10

<210> SEQ ID NO 48
<211> LENGTH: 22
<212> TYPE: PRT
<213> ORGANISM: Mus sp.

<400> SEQUENCE: 48

Glu Pro Ser Gly Pro Ile Ser Thr Ile Asn Pro Cys Pro Pro Cys Lys
1 5 10 15

Glu Cys His Lys Cys Pro
20

<210> SEQ ID NO 49
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (15)..(15)
<223> OTHER INFORMATION: Any amino acid except Cys
<220> FEATURE:
<221> NAME/KEY: MOD_RES
<222> LOCATION: (18)..(18)
<223> OTHER INFORMATION: Any amino acid except Cys
<220> FEATURE:
<221> NAME/KEY: MOD_RES
<222> LOCATION: (21)..(21)
<223> OTHER INFORMATION: Any amino acid except Cys

<400> SEQUENCE: 49

Glu Pro Ser Gly Pro Ile Ser Thr Ile Asn Pro Cys Pro Pro Xaa Lys
1 5 10 15

Glu Xaa His Lys Xaa Pro
20

<210> SEQ ID NO 50
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (12)..(12)
<223> OTHER INFORMATION: Any amino acid except Cys
<220> FEATURE:
<221> NAME/KEY: MOD_RES
<222> LOCATION: (18)..(18)
<223> OTHER INFORMATION: Any amino acid except Cys
<220> FEATURE:
<221> NAME/KEY: MOD_RES
<222> LOCATION: (21)..(21)
<223> OTHER INFORMATION: Any amino acid except Cys

<400> SEQUENCE: 50

Glu Pro Ser Gly Pro Ile Ser Thr Ile Asn Pro Xaa Pro Pro Cys Lys
1 5 10 15

Glu Xaa His Lys Xaa Pro
20

<210> SEQ ID NO 51
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<220> FEATURE:
<221> NAME/KEY: MOD_RES
<222> LOCATION: (12)..(12)
<223> OTHER INFORMATION: Any amino acid except Cys
<220> FEATURE:
<221> NAME/KEY: MOD_RES
<222> LOCATION: (15)..(15)
<223> OTHER INFORMATION: Any amino acid except Cys
<220> FEATURE:
<221> NAME/KEY: MOD_RES
<222> LOCATION: (21)..(21)
<223> OTHER INFORMATION: Any amino acid except Cys

<400> SEQUENCE: 51

```
Glu Pro Ser Gly Pro Ile Ser Thr Ile Asn Pro Xaa Pro Pro Xaa Lys
1               5                   10                  15

Glu Cys His Lys Xaa Pro
            20
```

<210> SEQ ID NO 52
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (12)..(12)
<223> OTHER INFORMATION: Any amino acid except Cys
<220> FEATURE:
<221> NAME/KEY: MOD_RES
<222> LOCATION: (15)..(15)
<223> OTHER INFORMATION: Any amino acid except Cys
<220> FEATURE:
<221> NAME/KEY: MOD_RES
<222> LOCATION: (18)..(18)
<223> OTHER INFORMATION: Any amino acid except Cys

<400> SEQUENCE: 52

```
Glu Pro Ser Gly Pro Ile Ser Thr Ile Asn Pro Xaa Pro Pro Xaa Lys
1               5                   10                  15

Glu Xaa His Lys Cys Pro
            20
```

<210> SEQ ID NO 53
<211> LENGTH: 12
<212> TYPE: PRT
<213> ORGANISM: Mus sp.

<400> SEQUENCE: 53

```
Glu Pro Ser Gly Pro Ile Ser Thr Ile Asn Pro Cys
1               5                   10
```

<210> SEQ ID NO 54
<211> LENGTH: 21
<212> TYPE: PRT
<213> ORGANISM: Mus sp.

<400> SEQUENCE: 54

```
Glu Pro Arg Val Pro Ile Thr Gln Asn Pro Cys Pro Pro Leu Lys Glu
1               5                   10                  15

Cys Pro Pro Cys Ala
            20
```

<210> SEQ ID NO 55
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (17)..(17)
<223> OTHER INFORMATION: Any amino acid except Cys
<220> FEATURE:
<221> NAME/KEY: MOD_RES
<222> LOCATION: (20)..(20)
<223> OTHER INFORMATION: Any amino acid except Cys

<400> SEQUENCE: 55

```
Glu Pro Arg Val Pro Ile Thr Gln Asn Pro Cys Pro Pro Leu Lys Glu
1               5                   10                  15

Xaa Pro Pro Xaa Ala
            20
```

<210> SEQ ID NO 56
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (11)..(11)
<223> OTHER INFORMATION: Any amino acid except Cys
<220> FEATURE:
<221> NAME/KEY: MOD_RES
<222> LOCATION: (20)..(20)
<223> OTHER INFORMATION: Any amino acid except Cys

<400> SEQUENCE: 56

```
Glu Pro Arg Val Pro Ile Thr Gln Asn Pro Xaa Pro Pro Leu Lys Glu
1               5                   10                  15

Cys Pro Pro Xaa Ala
            20
```

<210> SEQ ID NO 57
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (11)..(11)
<223> OTHER INFORMATION: Any amino acid except Cys
<220> FEATURE:
<221> NAME/KEY: MOD_RES
<222> LOCATION: (17)..(17)
<223> OTHER INFORMATION: Any amino acid except Cys

<400> SEQUENCE: 57

```
Glu Pro Arg Val Pro Ile Thr Gln Asn Pro Xaa Pro Pro Leu Lys Glu
1               5                   10                  15

Xaa Pro Pro Cys Ala
            20
```

-continued

<210> SEQ ID NO 58
<211> LENGTH: 11
<212> TYPE: PRT
<213> ORGANISM: Mus sp.

<400> SEQUENCE: 58

Glu Pro Arg Val Pro Ile Thr Gln Asn Pro Cys
1               5                   10

<210> SEQ ID NO 59
<211> LENGTH: 16
<212> TYPE: PRT
<213> ORGANISM: Mus sp.

<400> SEQUENCE: 59

Glu Pro Arg Ile Pro Lys Pro Ser Thr Pro Pro Gly Ser Ser Cys Pro
1               5                   10                  15

<210> SEQ ID NO 60
<211> LENGTH: 15
<212> TYPE: PRT
<213> ORGANISM: Mus sp.

<400> SEQUENCE: 60

Glu Pro Arg Ile Pro Lys Pro Ser Thr Pro Pro Gly Ser Ser Cys
1               5                   10                  15

<210> SEQ ID NO 61
<211> LENGTH: 5
<212> TYPE: PRT
<213> ORGANISM: Homo sapiens

<400> SEQUENCE: 61

Pro Lys Ser Cys Asp
1               5

<210> SEQ ID NO 62
<211> LENGTH: 5
<212> TYPE: PRT
<213> ORGANISM: Homo sapiens

<400> SEQUENCE: 62

Lys Ser Cys Asp Lys
1               5

<210> SEQ ID NO 63
<211> LENGTH: 5
<212> TYPE: PRT
<213> ORGANISM: Homo sapiens

<400> SEQUENCE: 63

Ser Cys Asp Lys Thr
1               5

<210> SEQ ID NO 64
<211> LENGTH: 5
<212> TYPE: PRT
<213> ORGANISM: Homo sapiens

<400> SEQUENCE: 64

Asp Lys Thr His Thr
1               5

<210> SEQ ID NO 65
<211> LENGTH: 5
<212> TYPE: PRT
<213> ORGANISM: Homo sapiens

<400> SEQUENCE: 65

Lys Thr His Thr Cys
1               5

<210> SEQ ID NO 66
<211> LENGTH: 5
<212> TYPE: PRT
<213> ORGANISM: Homo sapiens

<400> SEQUENCE: 66

Thr His Thr Cys Pro
1               5

<210> SEQ ID NO 67
<211> LENGTH: 5
<212> TYPE: PRT
<213> ORGANISM: Homo sapiens

<400> SEQUENCE: 67

His Thr Cys Pro Pro
1               5

<210> SEQ ID NO 68
<211> LENGTH: 5
<212> TYPE: PRT
<213> ORGANISM: Homo sapiens

<400> SEQUENCE: 68

Thr Cys Pro Pro Cys
1               5

<210> SEQ ID NO 69
<211> LENGTH: 5
<212> TYPE: PRT
<213> ORGANISM: Homo sapiens

<400> SEQUENCE: 69

Cys Pro Pro Cys Pro
1               5

<210> SEQ ID NO 70
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Ile Val Pro Arg Glu Cys
100

<210> SEQ ID NO 71
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Arg Arg Asn Gly Gly Ile Gly His Lys Cys
100 105

<210> SEQ ID NO 72
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 72

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Glu Lys
85 90 95

Lys Val Glu Arg Arg Asn Gly Gly Ile Gly His Lys Cys
100 105

<210> SEQ ID NO 73
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Gly Val Glu Arg Arg Asn Gly Gly Ile Gly His Lys Cys
            100                 105
```

<210> SEQ ID NO 74
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 74

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Glu Val Glu Arg Arg Asn Gly Gly Ile Gly His Lys Cys
            100                 105
```

<210> SEQ ID NO 75
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Glu Arg Asn Gly Gly Ile Gly His Lys Cys
100 105

<210> SEQ ID NO 76
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Glu Val Glu Arg Arg Gln Gly Gly Ile Gly His Lys Cys
100 105

<210> SEQ ID NO 77
<211> LENGTH: 5
<212> TYPE: PRT
<213> ORGANISM: Homo sapiens

<400> SEQUENCE: 77

Cys Asp Lys Thr His
1 5

<210> SEQ ID NO 78
<211> LENGTH: 8
<212> TYPE: PRT
<213> ORGANISM: Unknown
<220> FEATURE:
<221> NAME/KEY: source
<223> OTHER INFORMATION: /note="Description of Unknown: non-rodent hinge region peptide"

<400> SEQUENCE: 78

Glu Pro Lys Ser Cys Asp Lys Thr
1 5

<210> SEQ ID NO 79
<211> LENGTH: 10
<212> TYPE: PRT
<213> ORGANISM: Unknown
<220> FEATURE:
<221> NAME/KEY: source
<223> OTHER INFORMATION: /note="Description of Unknown: non-rodent hinge region peptide"

<400> SEQUENCE: 79

Glu Pro Lys Ser Cys Asp Lys Thr His Thr
1 5 10

<210> SEQ ID NO 80
<211> LENGTH: 9
<212> TYPE: PRT
<213> ORGANISM: Unknown
<220> FEATURE:
<221> NAME/KEY: source
<223> OTHER INFORMATION: /note="Description of Unknown: non-rodent hinge region peptide"

<400> SEQUENCE: 80

Glu Pro Lys Ser Cys Asp Lys Thr His
1 5

<210> SEQ ID NO 81
<211> LENGTH: 7
<212> TYPE: PRT
<213> ORGANISM: Unknown
<220> FEATURE:
<221> NAME/KEY: source
<223> OTHER INFORMATION: /note="Description of Unknown: non-rodent hinge region peptide"

<400> SEQUENCE: 81

Glu Pro Lys Ser Cys Asp Lys
1 5

<210> SEQ ID NO 82
<211> LENGTH: 6
<212> TYPE: PRT
<213> ORGANISM: Unknown
<220> FEATURE:
<221> NAME/KEY: source
<223> OTHER INFORMATION: /note="Description of Unknown: non-rodent hinge region peptide"

<400> SEQUENCE: 82

Glu Pro Lys Ser Cys Asp
1 5

<210> SEQ ID NO 83
<211> LENGTH: 4
<212> TYPE: PRT
<213> ORGANISM: Unknown
<220> FEATURE:
<221> NAME/KEY: source
<223> OTHER INFORMATION: /note="Description of Unknown: non-rodent hinge region peptide"

<400> SEQUENCE: 83

Glu Pro Lys Ser
1

```
<210> SEQ ID NO 84
<211> LENGTH: 3
<212> TYPE: PRT
<213> ORGANISM: Unknown
<220> FEATURE:
<221> NAME/KEY: source
<223> OTHER INFORMATION: /note="Description of Unknown:
      non-rodent hinge region peptide"

<400> SEQUENCE: 84

Glu Pro Lys
1


<210> SEQ ID NO 85
<211> LENGTH: 2
<212> TYPE: PRT
<213> ORGANISM: Unknown
<220> FEATURE:
<221> NAME/KEY: source
<223> OTHER INFORMATION: /note="Description of Unknown:
      non-rodent hinge region peptide"

<400> SEQUENCE: 85

Glu Pro
1


<210> SEQ ID NO 86
<211> LENGTH: 4
<212> TYPE: PRT
<213> ORGANISM: Homo sapiens

<400> SEQUENCE: 86

Asp Lys Lys Val
1


<210> SEQ ID NO 87
<211> LENGTH: 4
<212> TYPE: PRT
<213> ORGANISM: Homo sapiens

<400> SEQUENCE: 87

Asp Lys Arg Val
1


<210> SEQ ID NO 88
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Glu Lys Lys Val
1


<210> SEQ ID NO 89
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 89

Asp Lys Lys Ile
1

<210> SEQ ID NO 90
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 90

Asp Lys Gly Val
1

<210> SEQ ID NO 91
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 91

Asp Lys Glu Val
1

<210> SEQ ID NO 92
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(1)
<223> OTHER INFORMATION: Any amino acid except Cys
<220> FEATURE:
<221> NAME/KEY: MOD_RES
<222> LOCATION: (3)..(4)
<223> OTHER INFORMATION: Any amino acid except Cys

<400> SEQUENCE: 92

Xaa Lys Xaa Xaa
1

<210> SEQ ID NO 93
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 93

```
Glu Glu Arg Asn Gly Gly Ile Gly His Lys Cys
1               5                   10
```

<210> SEQ ID NO 94
<211> LENGTH: 5
<212> TYPE: PRT
<213> ORGANISM: Homo sapiens

<400> SEQUENCE: 94

Glu Pro Lys Ser Cys
1 5

<210> SEQ ID NO 95
<211> LENGTH: 11
<212> TYPE: PRT
<213> ORGANISM: Homo sapiens

<400> SEQUENCE: 95

Lys Val Asp Lys Lys Val Glu Pro Lys Ser Cys
1 5 10

<210> SEQ ID NO 96
<211> LENGTH: 11
<212> TYPE: PRT
<213> ORGANISM: Homo sapiens

<400> SEQUENCE: 96

Lys Val Asp Lys Arg Val Glu Pro Lys Ser Cys
1 5 10

<210> SEQ ID NO 97
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 97

Lys Val Asp Lys Lys Ile Val Pro Arg Glu Cys
1 5 10

<210> SEQ ID NO 98
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 98

Lys Val Asp Lys Lys Val Glu Arg Arg Asn Gly Gly Ile Gly His Lys
1 5 10 15

Cys

<210> SEQ ID NO 99
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 99

Lys Val Glu Lys Lys Val Glu Arg Arg Asn Gly Gly Ile Gly His Lys
1 5 10 15

Cys

-continued

<210> SEQ ID NO 100
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 100

Lys Val Asp Lys Gly Val Glu Arg Arg Asn Gly Gly Ile Gly His Lys
1 5 10 15

Cys

<210> SEQ ID NO 101
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 101

Lys Val Asp Lys Glu Val Glu Arg Arg Asn Gly Gly Ile Gly His Lys
1 5 10 15

Cys

<210> SEQ ID NO 102
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 102

Lys Val Asp Lys Lys Val Glu Glu Arg Asn Gly Gly Ile Gly His Lys
1 5 10 15

Cys

<210> SEQ ID NO 103
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 103

Lys Val Asp Lys Glu Val Glu Arg Arg Gln Gly Gly Ile Gly His Lys
1 5 10 15

Cys

<210> SEQ ID NO 104
<211> LENGTH: 61
<212> TYPE: PRT
<213> ORGANISM: Homo sapiens -continued

```
<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly
    50                  55                  60
```